(12) United States Patent
Nishikawa

(10) Patent No.: US 9,354,176 B2
(45) Date of Patent: *May 31, 2016

(54) METHOD FOR DETECTING A TARGET PARTICLE

(71) Applicant: OLYMPUS CORPORATION, Tokyo (JP)

(72) Inventor: Kazutaka Nishikawa, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/172,295

(22) Filed: Feb. 4, 2014

(65) Prior Publication Data

US 2014/0147854 A1 May 29, 2014

Related U.S. Application Data

(63) Continuation of application No. PCT/JP2012/060137, filed on Apr. 13, 2012.

(30) Foreign Application Priority Data

Aug. 11, 2011 (JP) ................................. 2011-175862

(51) Int. Cl.
   | | |
   |---|---|
   | *C12Q 1/68* | (2006.01) |
   | *G01N 21/64* | (2006.01) |
   | *G01N 21/27* | (2006.01) |
   | *G01N 21/76* | (2006.01) |

(52) U.S. Cl.
   CPC .......... *G01N 21/6486* (2013.01); *G01N 21/278* (2013.01); *G01N 21/645* (2013.01); *G01N 21/6428* (2013.01); *G01N 21/6452* (2013.01); *G01N 21/6458* (2013.01); *G01N 21/76* (2013.01); *G01N 2021/6417* (2013.01); *G01N 2021/6419* (2013.01); *G01N 2021/6421* (2013.01); *G01N 2021/6493* (2013.01)

(58) Field of Classification Search
   CPC .............. G01N 2021/6417; G01N 2021/6419; G01N 2021/6421; G01N 2021/6493; G01N 21/6428; G01N 21/6452; G01N 21/6486; G01N 21/76
   USPC .................................................. 435/91.2, 6.1
   See application file for complete search history.

(56) References Cited

U.S. PATENT DOCUMENTS

| | | | |
|---|---|---|---|
| 4,251,733 A | 2/1981 | Hirleman, Jr. | |
| 4,421,860 A | 12/1983 | Elings et al. | |
| 5,308,900 A | 5/1994 | Willcox | |
| 5,308,990 A | 5/1994 | Takahashi et al. | |
| 5,547,849 A | 8/1996 | Baer et al. | |
| 5,866,336 A | 2/1999 | Nazarenko et al. | |
| 6,280,960 B1 | 8/2001 | Carr | |
| 6,376,843 B1 | 4/2002 | Palo | |
| 6,388,746 B1 | 5/2002 | Eriksson et al. | |
| 6,388,788 B1 | 5/2002 | Harris et al. | |
| 6,400,487 B1 | 6/2002 | Harris et al. | |
| 6,403,338 B1 | 6/2002 | Knapp et al. | |
| 6,495,676 B1 | 12/2002 | Wood et al. | |
| 6,710,871 B1 | 3/2004 | Goix | |
| 6,782,297 B2 | 8/2004 | Tabor | |
| 6,856,391 B2 | 2/2005 | Garab et al. | |
| 6,927,401 B1 | 8/2005 | Palo | |
| 8,284,484 B2 | 10/2012 | Hoult et al. | |
| 2001/0035954 A1 | 11/2001 | Rahn et al. | |
| 2002/0008211 A1 | 1/2002 | Kask | |
| 2002/0036775 A1 | 3/2002 | Wolleschensky et al. | |
| 2003/0036855 A1 | 2/2003 | Harris et al. | |
| 2003/0218746 A1 | 11/2003 | Sampas | |
| 2004/0022684 A1 | 2/2004 | Heinze et al. | |
| 2004/0051051 A1 | 3/2004 | Kato et al. | |
| 2004/0150880 A1 | 8/2004 | Nakata et al. | |
| 2004/0152118 A1 | 8/2004 | Van Atta et al. | |
| 2005/0260660 A1 | 11/2005 | van Dongen et al. | |
| 2005/0277134 A1* | 12/2005 | Okano et al. ....................... 435/6 |
| 2006/0008799 A1 | 1/2006 | Cai et al. | |
| 2006/0078998 A1 | 4/2006 | Puskas et al. | |
| 2006/0158721 A1 | 7/2006 | Nakata et al. | |

(Continued)

FOREIGN PATENT DOCUMENTS

| | | |
|---|---|---|
| CN | 103620389 A | 3/2014 |
| EP | 1 906 172 A1 | 4/2008 |
| EP | 2216338 A1 | 8/2010 |
| EP | 2522988 A1 | 11/2012 |
| EP | 2543989 A1 | 1/2013 |
| EP | 2543990 A1 | 1/2013 |
| EP | 2584343 A1 | 4/2013 |
| EP | 2818850 A1 | 12/2014 |
| JP | 04-501956 A | 4/1992 |
| JP | 04-337446 A | 11/1992 |
| JP | 06113896 A | 4/1994 |
| JP | 2000-106876 A | 4/2000 |
| JP | 2002-507762 A | 3/2002 |

(Continued)

OTHER PUBLICATIONS

European Official Communication dated Nov. 20, 2014, issued in related EP Application No. 11812369.4 (5 pages).

(Continued)

*Primary Examiner* — Cynthia B Wilder
(74) *Attorney, Agent, or Firm* — Westerman, Hattori, Daniels & Adrian, LLP

(57) ABSTRACT

This method for detecting a target particle has: (a) a step for preparing a sample solution containing target particles and one type or two or more types of a luminescent probe that binds to the target particles, and allowing two or more molecules of the luminescent probe to bind per one molecule of the target particles in the sample solution, and (b) a step for calculating the number of molecules of target particles bound to the luminescent probe present in the sample solution prepared in step (a) by a scanning molecule counting method by using as an indicator thereof the strength of light signals of the individually detected particles, and the luminescent probe is one type or two or more types of a luminescent probe to which the same type of luminescent substance is bound.

5 Claims, 6 Drawing Sheets

(56) References Cited

U.S. PATENT DOCUMENTS

| | | | |
|---|---|---|---|
| 2006/0256338 | A1 | 11/2006 | Gratton et al. |
| 2007/0231808 | A1 | 10/2007 | Gouda et al. |
| 2008/0052009 | A1 | 2/2008 | Chiu et al. |
| 2008/0158561 | A1 | 7/2008 | Vacca et al. |
| 2009/0159812 | A1 | 6/2009 | Livingston |
| 2010/0033718 | A1 | 2/2010 | Tanaami |
| 2010/0177190 | A1 | 7/2010 | Chiang et al. |
| 2010/0202043 | A1 | 8/2010 | Ujike |
| 2010/0301231 | A1 | 12/2010 | Yamaguchi |
| 2011/0312841 | A1* | 12/2011 | Silverbrook et al. ........... 506/40 |

FOREIGN PATENT DOCUMENTS

| | | | |
|---|---|---|---|
| JP | 2002-543414 A | 12/2002 | |
| JP | 2004-506192 A | 2/2004 | |
| JP | 2004-121231 A | 4/2004 | |
| JP | 2004-187607 A | 7/2004 | |
| JP | 2005-098876 A | 4/2005 | |
| JP | 2005-099662 A | 4/2005 | |
| JP | 2005-308412 A | 11/2005 | |
| JP | 2006-333739 A | 12/2006 | |
| JP | 2007-020565 A | 2/2007 | |
| JP | 4023523 B2 | 12/2007 | |
| JP | 2008-058285 A | 3/2008 | |
| JP | 2008-116440 A | 5/2008 | |
| JP | 2008-536093 A | 9/2008 | |
| JP | 2008-292371 A | 12/2008 | |
| JP | 2008-298743 A | 12/2008 | |
| JP | 2009-145242 A | 7/2009 | |
| JP | 2009-250721 A | 10/2009 | |
| JP | 2009-281831 A | 12/2009 | |
| JP | 2009-288161 A | 12/2009 | |
| JP | 2010-019553 A | 1/2010 | |
| JP | 2010-190730 A | 9/2010 | |
| JP | 2011-002415 A | 1/2011 | |
| JP | 2011-033613 A | 2/2011 | |
| JP | 2011-036150 A | 2/2011 | |
| JP | 2011-508219 A | 3/2011 | |
| WO | 88/02785 A2 | 4/1988 | |
| WO | 90/06042 A2 | 6/1990 | |
| WO | 92/22671 A1 | 12/1992 | |
| WO | 98/16814 A | 4/1998 | |
| WO | 99/47963 A | 9/1999 | |
| WO | 00/52451 A1 | 9/2000 | |
| WO | 00/66985 A1 | 11/2000 | |
| WO | 00/71991 A1 | 11/2000 | |
| WO | 02/12864 A1 | 2/2002 | |
| WO | 2004/020675 A2 | 3/2004 | |
| WO | 2006/084283 A2 | 8/2006 | |
| WO | 2007/010803 A1 | 1/2007 | |
| WO | 2007/118209 A2 | 10/2007 | |
| WO | 2007/147159 A2 | 12/2007 | |
| WO | 2008/007580 A1 | 1/2008 | |
| WO | 2008/080417 A1 | 7/2008 | |
| WO | 2009/066447 A1 | 5/2009 | |
| WO | 2009/117033 A2 | 9/2009 | |
| WO | 2010/056579 A1 | 5/2010 | |
| WO | 2011/108369 A1 | 9/2011 | |
| WO | 2011/108370 A1 | 9/2011 | |
| WO | 2011/108371 A1 | 9/2011 | |
| WO | 2012/014778 A1 | 2/2012 | |

OTHER PUBLICATIONS

Shuming N. et al., "Real-Time Detection of Single Molecules in Solution by Confocal Fluorescence Microscopy", Analytical Chemistry, American Chemical Society, vol. 67, No. 17, pp. 2849-2857, (1995), cited in European Official Communication dated Nov. 20, 2014 (9 pages).

International Search Report dated on Jul. 24, 2012, issued in corresponding application No. PCT/JP2012/060137.

Kinjo, masataka, "Single molecule protein, nucleic acid, an d enzyme assays and thier procedures, single molecule detection by fluorescence correlation spectroscopy", Proteins, Nucleic Acids and Enzymes, 1999, vol. 44, No. 9, pp. 1431-1438, cited in Specification, w/English translation.

Myer-Almes, F., J., "Nanoparticle Immunoassays: A new Method for Use in Molecular Diagnostics and High Throughput Pharmaceutical Screening based on Fluorescence Correlation Spectroscopy", Springer-Verlag Berlin heidelberg, Germany, 2001, pp. 204-224, cited in Specification.

Kato, Norio, et al., "Genetic Dedicine", 2002, vol. 6, No. 2, pp. 271-277, cited in Specification, w/partial English translation.

Extended European Search Report dated Oct. 20, 2014, issued in related EP Application No. 12770835.2 (10 pages).

Park, Mira et al., "Counting the Number of Fluorophores Labeled in Biomolecules by Observing the Fluorescence-Intensity Transient of a Single Molecule", Bulletin of the Chemical Society of Japan, Aug. 30, 2005, vol. 78, No. 9, p. 1612-1618.

U.S. Office Action dated Apr. 2, 2013, issued in related U.S. Appl. No. 13/596,280 (7 pages).

Kask, Peet et al., "Two-Dimensional Fluorescence Intensity Distribution Analysis: Theory and Applications", Biophysical Journal, Apr. 2000, vol. 78, p. 1703-1713.

Chinese Office Action dated Aug. 13, 2013, issued in related Chinese application No. 201180011655.3; w/ English Translation (16 pages).

International Search Report dated Mar. 29, 2011, issued in related PCT/JP2011/053483.

International Preliminary Report on Patentability (PCT/IPEA/409) issued in related PCT/JP2011/053483.

Chinese Office Action dated Aug. 9, 2013, issued in related Chinese application No. 201180011640.7; w/ English Translation (16 pages).

International Search Report Mar. 29, 2011, issued in related PCT/JP2011/053482.

International Preliminary Report on Patentability (PCT/IPEA/409) issued in related PCT/JP2011/053482.

Sasaki, Shigeki, "Creation of Functional Recognition Molecules for Chemical Modification of Gene Expression", Yakugaku Zasshi, the Pharmaceutical Society of Japan, 2002, vol. 122, No. 12, p. 1081-1093.

Chinese Office Action dated Feb. 7, 2013, issued in related Chinese application No. 201180011644.5; w/ English Translation (19 pages).

Extended European Search Report dated Mar. 28, 2013, issued in related EP application No. 11750481.1 (6 pages).

International Search Report dated Mar. 29, 2011, issued in related PCT/JP2011/053481.

International Preliminary Report on Patentability (PCT/IPEA/409) issued in related PCT/JP2011/053481.

Goodwin, Peter et al., "Rapid Sizing of Individual Fluorescently Stained DNA Fragments by Flow Cytometry", Nucleic Acids Research, 1993, vol. 21, No. 4, p. 803-806.

Keller, Richard et al., "Single-Molecule Fluorescence Analysis in Solution", Applied Spectroscopy, 1996, vol. 50, No. 7, p. 12A-32A.

Lee, Yuan-Hsiang et al., "Laser-Induced Fluorescence Detection of a Single Molecule in a Capillary", Analytical Chemistry, Dec. 1, 1994, vol. 66, No. 23, p. 4142-4149.

Li, Haitao et al., "Ultrasensitive Coincidence Fluorescence Detection of Single DNA Molecules", Analytical Chemistry, Apr. 1, 2003, vol. 75, No. 7, p. 1664-1670.

Nie, Shuming et al., "Probing Individual Molecules with Confocal Fluorescence Microscopy", Science, Nov. 11, 1994, vol. 266, p. 1018-1021.

Tahari, Abdel. "Fluorescence Correlation Spectroscopy: Ultrasensitive Detection in Clear and Turbid Media", University of Illinois, 2006, p. 1-88.

Wu, Alan et al., "Development and Preliminary Clinical Validation of a High Sensitivity Assay for Cardiac Troponin Using a Capillary Flow (Single Molecule) Fluorescence Detector", Clinical Chemistry, 2006, vol. 52, No. 11, p. 2157-2159.

Itoh et al., "A New Method for Detection of Influenza Viruses by Single Particle-Recognition Based on the Principle of Fluorescence Correlation Spectroscopy", Chemistry and Biology, 2009, vol. 47, No. 12, p. 823-830; with English summary.

Carlsson, K. et al., "Three-dimensional Microscopy Using a Confocal Laser Scanning Microscope", Optics Letters, Optical Society of America, Feb. 1985, vol. 10, No. 2, p. 53-55, XP007922413.

(56) References Cited

OTHER PUBLICATIONS

U.S. Office Action dated Oct. 4, 2013, issued in related U.S. Appl. No. 13/596,243 (7 pages).
Japanese Office Action dated Dec. 18, 2012, issued in related JP application No. 2012-503060; w/ English Translation (6 pages).
Yoshimura, Yoshinaga et al., "Development of Template-Directed Reversible DNA Photocrosslinking", Nucleic Acids Symposium Series, 2008, vol. 10, No. 52, p. 423-424.
Yoshimura, Yoshinaga et al., "Ultrafast Reversible Photo-Cross-Linking Reaction: Toward in Situ DNA Manipulation", Organic Letters, 2008, vol. 10, No. 15, p. 3227-3230.
Takasugi, M. et al., "Sequence-Specific Photo-Induced Cross-Linking of the Two Strands of Double-Helical DNA by a Psoralen Covalently Linked to a Triple Helix-Forming Oligonucleotide", Proc. Natl. Acad. Sci. USA, Jul. 1991, vol. 88, p. 5602-5606.
Kask, Peet et al. "Flourescence-Intensity Distribution Analysis and its Application in Biomolecular Detection Technology", PNAS, Nov. 23, 1999, vol. 96, No. 24, p. 13756-13761.
U.S. Office Action dated Jan. 3, 2013, issued in co-pending U.S. Appl. No. 13/597,825.
U.S. Notice of Allowance dated Jun. 19, 2013, issued in U.S. Appl. No. 13/596,280.
Kato, N. et al., "A Single Molecule Analyzer that Enables New Analysis of DNA and Protein Interactions", Gene Medicine, 2002, vol. 6, No. 2, p. 271-277 with partial translation; with English summary.
Sando, Shinsuke et al., "Quencher as Leaving Group: Efficient Detection of DNA-Joining Reactions", Journal of the American Chemical Society, 2002, vol. 124, No. 10, p. 2096-2097.
International Search Report dated Sep. 20, 2011, issued in related PCT/JP2011/066576 (6 pages).
U.S. Office Action dated Feb. 20, 2014, issued in related U.S. Appl. No. 13/746,968 (11 pages).
U.S. Notice of Allowance dated Mar. 27, 2013, issued in related U.S. Appl. No. 13/597,825 (8 pages).
U.S. Office Action dated May 22, 2014, issued in related U.S. Appl. No. 13/746,968 (10 pages).
International Search Report dated Apr. 23, 2013, issued in related PCT/JP2013/053080 (4 pages).
International Search Report dated Jul. 24, 2012, issued in related PCT/JP2012/060137 (6 pages).
International Search Report dated Aug. 7, 2012, issued in related PCT/JP2012/066576 (4 pages).
International Search Report dated Mar. 5, 2013, issued in related PCT/JP20121081350 (2 pages).
Chinese Office Action dated Jul. 14, 2014, issued in related Chinese application No. 201180036710.4; w/ English Translation (12 pages).
Meyer-Almes, F.J., "Nanoparticle Immunoassays: A new Method for Use in Molecular Diagnostics and High Throughput Pharmaceutical Screening based on Fluorescence Correlation Spectroscopy", Springer-verlag, Berlin heldelberg, Germany, 2001, pp. 204-224, cited in specification.
U.S. Notice of Allowance dated Dec. 24, 2013, issued in U.S. Appl. No. 13/596,243.
Notice of Reasons for Rejection dated May 19, 2015, issued in corresponding Japanese Patent Application No. 2012-526460 with English translation (8 pages).
Hebert et al., "Spatiotemporal Image Correlation Spectroscopy (STICS) Theory, Verification, and Application to Protein Velocity Mapping in Living CHO Cells", Biophysical Journal, May 2005, vol. 88, No. 5, pp. 3601-3614, cited in Extended European Search Report dated Mar. 26, 2015 (14 pages).
Extended European Search Report dated Mar. 26, 2015, issued in corresponding EP Patent Application No. 12821897.1 (13 pages).
Office Action dated Mar. 25, 2015, issued in Chinese Patent Application No. 201180036710.4, with English translation (8 pages).
Chinese Office Action dated Apr. 20, 2015, issued in Chinese Patent Application No. 2012800412706 with English translation (11 pages).
Extended European Search Report dated May 20, 2015, issued in European Patent Application No. 12828423.9 (18 pages).
Communication pursuant to Article 94(3) dated May 13, 2015, issued in European Patent Application No. 11 812 369.4 (5 pages).
U.S. Office Action dated Apr. 13, 2015, issued in U.S. Appl. No. 13/746,968 (19 pages).
Non-Final Office Action dated Sep. 28, 2015, issued in U.S. Appl. No. 14/322,010 (10 pages).
Final Office Action dated Sep. 28, 2015, issued in U.S. Appl. No. 13/746,968 (24 pages).
Extended European Search Report issued Feb. 16, 2016 in EP 13764425.8.
Advisory Action mailed Feb. 2, 2016, issued in U.S. Appl. No. 13/746,968.
Official Notice dated Nov. 30, 2015, issued in European application No. 11812369.4.
Prasad V et al. "Topical Review; Confocal microscopy of colloids", Journal of Physics: Condensed Matter, Institute of Physics Publishing, Bristol, GB, vol. 19, No. 11, Mar. 21, 2007, p. 113102.

* cited by examiner

METHOD FOR DETECTING A TARGET PARTICLE

The present application claims priority on the basis of Japanese Patent Application No. 2011-175862, filed in Japan on Aug. 11, 2011, the contents of which are incorporated herein by reference. The present application is a U.S. continuation application based on the PCT International Patent Application, PCT/JP2012/060137, filed on Apr. 13, 2012; the contents of which are incorporated herein by reference.

FIELD OF THE INVENTION

The present invention relates to a method for detecting a target particle labeled with a luminescent probe using an optical system capable of detecting light from a microregion in a solution, such as an optical system of a confocal microscope and multi-photon microscope.

DESCRIPTION OF THE RELATED ART

Due to progress made in the field of optical measurement technology in recent years, it has become possible to detect and measure feint light at the level of a single photon or single fluorescent molecule using the optical system of a confocal microscope and ultra-high-sensitivity photodetection technology capable of performing photon counting (detecting individual photons). Various devices or methods have been proposed that detect interactions between molecules such as biomolecules or coupling and dissociation reactions between molecules using the aforementioned feint light measurement technology. For example, fluorescence correlation spectroscopy (FCS: see, for example, Japanese Unexamined Patent Application, First Publication No. 2005-098876; Japanese Unexamined Patent Application, First Publication No. 2008-292371; Kinjo, M., Proteins, Nucleic Acids and Enzymes, 1999, Vol. 44, No. 9, pp. 1431-1438; Meyer-Alms, Fluorescence Correlation Spectroscopy, R. Rigler, ed., Springer, Berlin, 2000, pp. 204-224; Katoh, N., et al., Gene and Medicine, 2002, Vol. 6, No. 2, pp. 271-277) has been proposed. In the aforementioned method, fluorescence intensity is measured from fluorescent molecules or fluorescent-labeled molecules (such as fluorescent molecules) entering and leaving a microregion (confocal region where laser light of a microscope is focused; referred to as confocal volume) in a sample solution using the optical system of a laser confocal microscope and photon counting technology. In addition, information such as the speed of movement, size or concentration of fluorescent molecules and the like is obtained based on the average retention time (transitional diffusion time) of fluorescent molecules and the like in the microregion and the average value of the number of molecules remaining therein determined from the value of an autocorrelation function of measured fluorescence intensity. In addition, various phenomena in the manner of changes in molecular structure or size, molecule coupling and dissociation reactions or dispersion and aggregation can be detected. In addition, fluorescence intensity distribution analysis (FIDA: see, for example, Japanese Patent (Granted) Publication No. 4023523) and photon counting histograms (PCH: see, for example, International Publication No. WO 2008-080417) have been proposed. In the aforementioned methods, a histogram is generated of the fluorescence intensity of fluorescent molecules and the like entering and leaving a measured confocal volume in the same manner as FCS, and a statistical model formula is fit to the distribution of that histogram. As a result, the average value of the characteristic brightness of the fluorescent molecules and the like and the average value of the number of molecules remaining in the confocal volume are calculated, and changes in molecular structure and size, coupling and/or dissociation, dispersion or aggregation and the like are then estimated based on this information. Moreover, Japanese Unexamined Patent Application, First Publication No. 2007-20565, and Japanese Unexamined Patent Application, First Publication No. 2008-116440 propose a method for detecting a fluorescent substance based on the time lapse of a fluorescent signal of a sample solution measured using the optical system of a confocal microscope. Japanese Unexamined Patent Application, First Publication No. H04-337446 proposes a signal arithmetic processing technology for detecting the presence of fluorescent fine particles in a flow or on a substrate by measuring feint light from fluorescent fine particles that have passed through a flow cytometer or fluorescent fine particles immobilized on a substrate using photon counting technology.

In particular, according to methods using microregion fluorescence measurement technology using the optical system of a confocal microscope and photon counting technology in the manner of FCS or FIDA and the like, the sample required for measurement is only required to be at an extremely low concentration and in an extremely small amount in comparison with conventional methods (since the amount used for a single measurement is roughly only several tens of microliters). In addition, according to the aforementioned methods, measurement time is shortened considerably (measurement of a duration on the order of several seconds for a single measurement is repeated several times). Thus, these technologies are expected to make it possible to carry out experimentation or testing less expensively and more rapidly in comparison with conventional biochemical methods in the case of performing analyses on scarce or expensive samples frequently used in fields such as medical or biochemical research and development, or in the case of a large number of specimens such as when clinically diagnosing diseases or screening physiologically active substances.

On the other hand, in methods that detect by FIDA and the like by labeling a detection target in the form of target particles with a luminescent probe, in the case both a luminescent probe that binds with a target particle and a luminescent probe that does not bind with a target particle are present in a solution, it is important to be able to detect the target particle while distinguishing between the two. In Japanese Unexamined Patent Application, First Publication No. 2009-250721, for example, FIDA is carried out in the presence of a discoloration preventing agent using a luminescent probe labeled with a fluorescent dye that is easily discolored by reacting with a radical. As a result, a detection method is disclosed that provides a difference between fluorescence intensity detected from the luminescent probe bound to a target particle and fluorescence intensity detected from a luminescent probe not bound to a target particle, thereby distinguishing between the two.

In addition, Japanese Unexamined Patent Application, First Publication No. 2000-106876 discloses a method for amplifying a signal from a luminescent probe by binding a plurality of luminescent probes to a single target particle using the binding reaction between a ligand and a receptor, for example.

SUMMARY OF THE INVENTION

The inventors of the present invention completed the present invention as described below as a result of conducting extensive studies to solve the problems of prior art. In the case of indirectly detecting a particle dispersed and randomly moving in a sample solution by using as an indicator thereof light emitted from a luminescent probe bound to the particle, the particle bound to the luminescent probe is detected using a scanning molecule counting method. As a result, even in the case the concentration of the target particle in the sample solution is extremely low, the particle bound to the luminescent probe was found to be able to be detected with favorable sensitivity. Moreover, a plurality of luminescent probes is bound to the target particle. As a result, the target particle can be detected by distinguishing between a luminescent probe bound to the target particle and a free luminescent probe without having to preliminarily remove the free luminescent probe not bound to the target particle from the sample solution.

The scanning molecule counting method refers to a novel optical analysis technology proposed by the applicant of the present application in Japanese Patent Application No. 2010-044714.

Namely, the present invention has the following aspects:

(1) a method for detecting a target particle dispersed and moving randomly in a sample solution, comprising:

(a) preparing a sample solution containing the target particle and one type or two or more types of a luminescent probe that binds to the target particle, and allowing two or more molecules of the luminescent probe to bind per one molecule of the target particle in the sample solution, and (b) calculating the number of molecules of the target particle bound to the luminescent probe present in the sample solution prepared in (a);

the luminescent probe is one type or two or more types of a luminescent probe to which the same type of luminescent substance is bound, and the calculating of the number of molecules of target particles bound to the luminescent probe in (b) is carried out by, using an optical system of a confocal microscope or multi-photon microscope:

moving a location of a photodetection region of the optical system in the sample solution, detecting fluorescence released from the target particle in the photodetection region while moving the location of the photodetection region of the optical system in the sample solution, individually detecting the target particles by individually detecting a light signal released from the individual target particle from the detected light, and counting the number of the target particles detected during movement of the location of the photodetection region by counting only those particles for which two or more molecules of the luminescent probe are contained per particle by using as an indicator thereof the strength of a light signal of the individually detected particles;

(2) the method for detecting a target particle described in (1) above, wherein, in the moving of the location of the photodetection region, the location of the photodetection region is moved at a prescribed speed;

(3) the method for detecting a target particle described in (1) or (2) above, wherein, in the moving of the location of the photodetection region, the location of the photodetection region is moved at a speed that is faster than the diffusion movement speed of target particles bound to the luminescent probe;

(4) the method for detecting a target particle described in any of (1) to (3) above, wherein, in the individually detecting of the target particles by detecting a light signal from the individual target particle bound to the luminescent probe from the detected light, the entry of a single target particle bound to the luminescent probe into the photodetection region is detected based on the form of a chronologically detected light signal; and, (5) the method for detecting a target particle described in any of (1) to (4) above, wherein the luminescent probe is comprises a labeling probe that binds with the target particle and a luminescent substance of which one or two or more molecules thereof bind per one molecule of the labeling probe.

DETAILED DESCRIPTION OF THE PREFERRED EMBODIMENTS

Figure 1A:
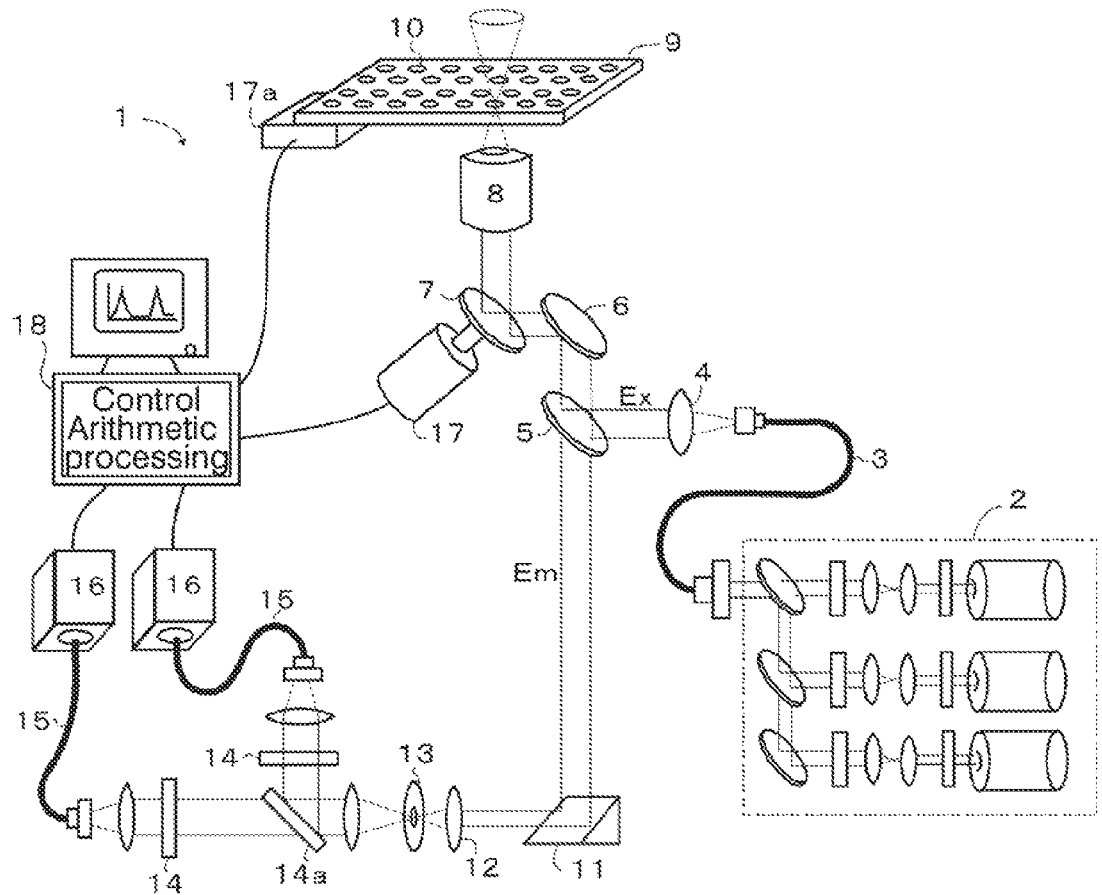
FIG. 1A is a schematic diagram of the internal structure of an optical analysis device for a scanning molecule counting method.

An explanation is first provided of the scanning molecule counting method. Light-emitting particles that disperse and move randomly in a sample solution (referring to the aforementioned "luminescent particles") cross a microregion while scanning the sample solution by microregions. Light emitted from the luminescent particles in a microregion is detected at this time. As a result, the luminescent particles can be counted or information relating to concentration or number density of the luminescent particles in the sample solution can be acquired by individually detecting each luminescent particle in the sample solution. In the aforementioned technology, the amount of sample required for measurement may be an extremely small amount (for example, on the order of only several tens of microliters) in the same manner as optical analysis technologies such as FIDA. In addition, measurement time is short. In addition, properties such as the concentration or number density of the luminescent particles can be quantitatively detected at a lower concentration or number density in comparison with optical analysis technologies such as FIDA.

Furthermore, luminescent particles refer to particles that emit light by fluorescence, phosphorescence, chemiluminescence, bioluminescence or light scattering and the like. In the method for detecting a target particle of the present embodiment, particles to which target particles and a luminescent probe are bound are luminescent particles.

In the present embodiment, a "photodetection region" of a confocal microscope or multi-photon microscope refers to a microregion in which light is detected by those microscopes. In the case illumination light is reflected from an object lens, a "photodetection region" corresponds to the region where that illumination light is focused. Furthermore, this region is defined by the positional relationship between the object lens and pinhole in a confocal microscope in particular.

Light is successively detected while moving the location of the photodetection region in a sample solution, or in other words, while scanning the sample solution by photodetection regions. When the photodetection region being moved contains a luminescent probe bound to or associated with a randomly moving particle, light from the luminescent probe is detected. As a result, the presence of a single particle is detected (although depending on the mode of the experiment, the luminescent probe may also dissociate from the particle desired to be detected (target particle) during detection of light after having bound to that particle). Light signals from the luminescent probe are individually detected in the successively detected light. As a result, the presence of an individual particle (a particle bound to the luminescent probe) is successively detected, and various information relating to the state of the particles in the solution is acquired. More specifically, in the aforementioned configuration, the number of particles detected during movement of the location of the photodetection region may also be counted, for example, by counting individually detected particles (particle counting). According to the aforementioned configuration, information relating to number density or concentration of particles in a sample solution is obtained by combining the number of particles and the amount of movement of the location of the photodetection region. In particular, particle number density or concentration can be specifically determined by, for example, moving the location of the photodetection region at a prescribed speed by an arbitrary method, and specifying the total volume of the movement locus of the location of the photodetection region. Naturally, instead of determining absolute values for number density or concentration directly, a relative ratio of number density or concentration may also be determined relative to a plurality of sample solutions or reference sample solutions having a standard concentration or number density. In addition, in the scanning molecule counting method, a configuration is employed in which the location of the photodetection region is moved by changing the light path of the optical system. Consequently, movement of the photodetection region is rapid, and mechanical vibrations or actions attributable to fluid dynamics do not substantially occur in the sample solution. Consequently, light can be measured with the particles targeted for detection in a stable state without particles targeted for detection being affected by dynamic action (if vibrations or flow act in the sample solution, the physical properties of the particles may change). It is also not necessary to provide a configuration that allows a sample solution to flow there through. Consequently, measurements and analyses can be carried out on an extremely small amount of sample solution (on the order of one to several tens of microliters) in the same manner as in the case of FCS or FIDA and the like.

In the aforementioned individually detecting of particles, a judgment as to whether or not a luminescent probe bound to a single particle (including the case in which a single luminescent probe is bound to a single particle, the case in which a plurality of luminescent probes is bound to a single particle, and the case in which a luminescent probe has dissociated from a particle after having bound to a single particle according to the experimental mode, and to apply similarly hereinafter) has entered the photodetection region based on successively detected light signals may be carried out based on the form of a chronologically detected light signal. Furthermore, in this embodiment, the entry of a luminescent probe bound to a single particle into the photodetection region may typically be detected when a light signal is detected that has greater strength than a prescribed threshold value.

In addition, in the aforementioned moving of the location of the photodetection region, the movement speed of the location of the photodetection region in a sample solution may be suitably changed based on the properties of the luminescent probe bound to a particle or the number density or concentration thereof in a sample solution. As is understood by a person with ordinary skill in the art, the mode of light detected from the luminescent probe bound to a particle can be changed according to the properties thereof or the number density or concentration in a sample solution. In particular, the amount of light obtained from a luminescent probe bound to a single particle decreases as the movement speed of the photodetection region increases. Consequently, the movement speed of the photodetection region may be suitably changed so that light from the luminescent probe bound to a single particle can be measured with favorable accuracy and sensitivity.

Moreover, in the aforementioned moving of the location of the photodetection region, the movement speed of the location of the photodetection region in a sample solution may be set to be faster than the diffusion movement speed (average speed of particles moving by Brownian movement) of the luminescent probe bound to a particle to be detected (namely, a luminescent probe in a state of being bound to a target particle in the method for detecting a target particle of the present invention). As was previously described, in the scanning molecule counting method, light emitted from a luminescent probe bound to a single particle is detected when a photodetection region has passed through a location where that luminescent probe is present, thereby resulting in individual detection of the luminescent probe. However, in the case the luminescent probe bound to a particle moves randomly through a solution by Brownian movement and enters and leaves the photodetection region a plurality of times, light signals (light signals indicating the presence of a particle desired to be detected) are detected a plurality of times from a single luminescent probe. Consequently, it becomes difficult to make a detected light signal correspond to the presence of a single particle desired to be detected. Thus, the movement speed of the photodetection region is set to be faster than the diffusion movement speed of the luminescent probe bound to a particle (and more specifically, the movement speed of the photodetection region is set so as to be moved at a speed faster than the diffusion movement speed of a luminescent probe in a state of being bound to a target particle). As a result, a luminescent probe bound to a single particle can be made to correspond to a single light signal (a light signal representing the presence of a particle). Furthermore, diffusion movement speed varies according to the luminescent probe bound to a particle. Consequently, the movement of the photodetection region may be suitably changed corresponding to the properties (and particularly, the diffusion constant) of the luminescent probe bound to a particle.

Changing of the light path of the optical system used to move the location of the photodetection region may be carried out by an arbitrary method.

For example, the location of the photodetection region may be changed by changing the light path using a galvanometer mirror employed in laser scanning optical microscopes. The movement locus of the location of the photodetection region may be set arbitrarily, and can may be selected from among, for example, a circular, oval, rectangular, linear or curved locus.

In the scanning molecule counting method, the photodetection mechanism per se is composed so as to detect light from a photodetection region of a confocal microscope or multi-photon microscope in the same manner as in the case of optical analysis technologies such as FIDA. Consequently, the amount of sample solution may also similarly be an extremely small amount. However, in the scanning molecule counting method, statistical processing involving calculation of fluctuations in fluorescence intensity and the like is not carried out. Consequently, in the optical analysis technology employing the scanning molecule counting method, a sample solution can be applied in which the number density or concentration of particles is considerably lower than the level required by conventional optical analysis technologies such as FIDA.

In addition, in the scanning molecule counting method, each particle dispersed or dissolved in a solution is detected individually. Consequently, counting of particles, determination of particle concentration or number density in a sample solution, or acquisition of information relating to concentration or number density, can be carried out quantitatively using that information. Namely, according to the scanning molecule counting method, a particle is detected one at a time by creating a 1:1 correlation between a particle passing through a photodetection region and a detected light signal. Consequently, particles dispersed and moving randomly in a solution can be counted. In addition, the concentration or number density of particles in a sample solution can be determined more accurately in comparison with conventional methods. In actuality, according to the method for detecting a target particle of the present embodiment comprising individually detecting a luminescent probe bound to a target particle and then counting the number thereof to determine particle concentration, the target particle can be detected even if the concentration of a luminescent probe bound to target particle in a sample solution is lower than the concentration able to be determined based on fluorescence intensity as measured with a fluorescence spectrophotometer or plate reader.

Moreover, according to an aspect in which a sample solution is scanned by photodetection regions by changing the light path of the optical system, the interior of the sample solution is observed uniformly or the sample solution is observed in a mechanically stable state without imparting mechanical vibrations or actions attributable to fluid dynamics to the sample solution. Consequently, the reliability of quantitative detection results is improved in comparison with the case of causing the generation of flow in a sample (in the case of imparting flow to a sample, in addition to it being difficult to impart a uniform flow at all times, the configuration of the device becomes complex, and together with causing a considerable increase in the amount of sample required, the particles in solution, luminescent probe, complex thereof or other substances may undergo deterioration or degeneration due to fluid dynamic action generated by that flow). In addition, measurements can be carried out in a state that does not impart effects caused by dynamic action or artifacts on particles to be detected in a sample solution.

<Configuration of Optical Analysis Device for Scanning Molecule Counting Method>

Figure 1B:
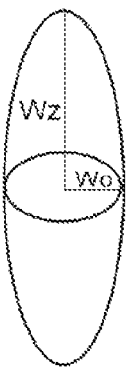
FIG. 1B is a schematic diagram of a confocal volume (observation region of a confocal microscope).

As schematically exemplified in FIG. 1A, the scanning molecule counting method can be realized in a basic configuration thereof by an optical analysis device composed by combining the optical system of a confocal microscope capable of performing FCS or FIDA and the like with a photodetector. As shown in FIG. 1A, an optical analysis device 1 is composed of optical system components 2 to 17, and a computer 18 for controlling the operation of each component of the optical systems and acquiring and analyzing data. The optical system of the optical analysis device 1 may be composed in the same manner as the optical system of an ordinary confocal microscope. In the aforementioned optical system, laser light (Ex) that has propagated from a light source 2 through a single-mode optic fiber 3 is radiated in the form of light that diverges at an angle determined according to a characteristic NA at the outgoing end of the fiber, is converted to parallel light by a collimator 4, and is reflected by a dichroic mirror 5 and reflecting mirrors 6 and 7, after which it enters an object lens 8. A microplate 9, in which are arranged sample containers or wells 10 into which are dispensed one to several tens of microliters of a sample solution, is typically arranged above the object lens 8. Laser light emitted from the object lens 8 is focused on the sample solution in the sample containers or wells 10, forming a region of high light intensity (excitation region). Targeted particles, a luminescent probe that binds to the particle, and typically a molecule having a luminescent label such as a fluorescent dye added thereto, are dispersed or dissolved in the sample solution. When a particle bound to or associated with the luminescent probe (or a luminescent probe that has dissociated from the particle after having initially bound thereto depending on the mode of the experiment) enters the excitation region, light excited by the luminescent probe is released during that time. The released light (Em) passes through the object lens 8 and dichroic mirror 5, is reflected by a mirror 11, and is concentrated by a condenser lens 12. Subsequently, the concentrated light (Em) passes through a pinhole 13 followed by passing through a barrier filter 14 (where only light components of a specific wavelength band are selected), after which it is introduced into a multi-mode optic fiber 15 and reaches a photodetector 16 where it is converted to a time series electrical signal. Subsequently, the converted electrical signal is input to the computer 18 where processing for optical analysis is carried out by an aspect to be subsequently explained. Furthermore, in the aforementioned configuration, the pinhole 13 is arranged at a location conjugate to the focal position of the object lens 8. As a result, only light emitted from the focused region of the laser light as schematically shown in FIG. 1B, namely light emitted from the excitation region, passes through the pinhole 13, while light from a location other than the excitation region is blocked. The focused region of the laser light shown in FIG. 1B is normally a photodetection region in the present optical analysis device having an effective volume of about 1 fL to 10 fL (and typically has a Gaussian distribution or Lorentzian distribution in which light intensity reaches a peak in the center of the region, and effective volume is the volume of a roughly ellipsoidal shape in which the boundary of light intensity is plane defined as 1/e2). The aforementioned focused region is also referred to as confocal volume. In addition, in the scanning molecule method, light is detected from light from a complex consisting of a single particle and luminescent probe or a luminescent probe, and for example, feint light is detected from one or a plurality of fluorescent dye molecules. Consequently, an ultra-high-sensitivity photodetector capable of use in photon counting may be used for the photodetector 16. In addition, the stage of the microscope (not shown) may be provided with a stage position adjustment device 17a for moving the position of the microplate 9 in the horizontal direction in order to change the well 10 to be observed. Operation of the stage position adjustment device 17a may be controlled by the computer 18. As a result of employing the aforementioned configuration, measurements can be carried out rapidly even in the case of multiple specimens.

Figure 1C:
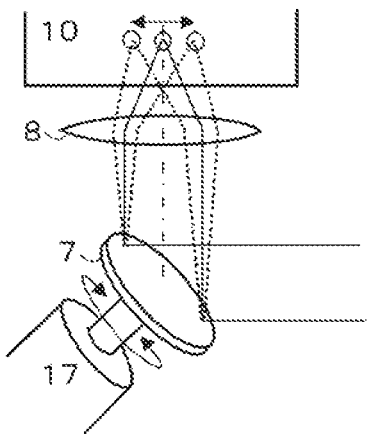
FIG. 1C is a schematic diagram of a mechanism for moving the location of a photodetection region in a sample solution by changing the orientation of a mirror.

Moreover, in the optical system of the aforementioned optical analysis device, a mechanism is provided for scanning the sample solution by photodetection regions by changing the light path of the optical system, namely a mechanism for moving the location of the focused region (photodetection region) in the sample solution. A mirror light deflector 17 that changes the orientation of the reflecting mirror 7, for example, may be employed as a mechanism for moving the location of the photodetection region in this manner as schematically exemplified in FIG. 1C. This mirror light deflector 17 may be composed in the same manner as a galvanometer mirror device provided in ordinary laser scanning optical microscopes. In addition, the mirror light defector 17 is driven in coordination with light detection by the photodetector 16 under the control of the computer 18 so as to achieve a desired movement pattern of the location of the photodetection region. The movement locus of the location of the photodetection region is arbitrarily selected from among a circular, oval, rectangular, linear and curved locus or a combination thereof (and various movement patterns may be able to be selected with a program installed in the computer 18). Furthermore, although not shown in the drawings, the location of the photodetection region may be moved in the vertical direction by moving the object lens 8 up and down. According to a configuration that moves the location of the photodetection region by changing the light path of the optical system instead of moving a sample solution, there is no substantial occurrence of mechanical vibrations or actions attributable to fluid dynamics in the sample solution. Thus, effects of dynamic action on a target can be eliminated, thereby making it possible to carry out stable measurements.

In the case a conjugate of a particle and luminescent probe or a luminescent probe emits light as a result of multi-photon absorption, the aforementioned optical system is used in the form of a multi-photon microscope. In that case, since light is only released in the focused region of the excitation light (photodetection region), the pinhole 13 may be omitted. In addition, in the case a conjugate of a particle and luminescent probe or a luminescent probe emits light by chemiluminescence or bioluminescent phenomena without depending on excitation light, optical system components 2 to 5 for generating excitation light may be omitted. In the case a conjugate of a particle and luminescent probe or a luminescent probe emits light by phosphorescence or light scattering, the aforementioned optical system of a confocal microscope is used as is. Moreover, in the optical analysis device 1, a plurality of excitation light sources 2 are provided. In addition, the wavelength of the excitation may be suitably selected according to the wavelength of light that excites a conjugate of a particle and luminescent probe or a luminescent probe. Similarly, a plurality of photodetectors 16 is provided. In addition, in the case a plurality of types of conjugates of a particle and luminescent probe or a plurality of luminescent probes having different wavelengths are contained in a sample, the light emitted therefrom may be detected separately according to wavelength.

<Principle of Optical Analysis Technology of Scanning Molecule Counting Method>

In comparison with conventional biochemical analysis technologies, spectral analysis technologies such as FIDA are superior in that they require only an extremely small amount of sample and allow testing to be carried out rapidly. However, in the case of spectral analysis technologies such as FIDA, the concentration and properties of target particles are in principle determined based on fluctuations in fluorescence intensity. Consequently, in order to obtain measurement results of favorable accuracy, the concentration or number density of target particles in a sample solution is required to be of a level such that roughly one target particle is present at all times in a photodetection region CV during measurement of fluorescence intensity, and such that significant light intensity (photon count) is detected at all times during the measurement time. If the concentration or number density of the target particles is lower than that level, such as in the case of being at a level such that a target particle only occasionally enters the photodetection region CV, significant light intensity (photon count) only appears during a portion of the measurement time. As a result, it becomes difficult to accurately determine fluctuations in light intensity. In addition, in the case the concentration of target particles is considerably lower than the level at which roughly one target particle is present in the photodetection region at all times during measurement, determination of fluctuations in light intensity are subject to the background effects. As a result, measurement time for obtaining an amount of significant light intensity data sufficient for making a determination is prolonged. In contrast, in the scanning molecule counting method, the concentration, number density or other properties of target particles can be detected even in the case the concentration of target particles is lower than the level required by spectral analysis technologies such as FIDA.

Figure 2A:
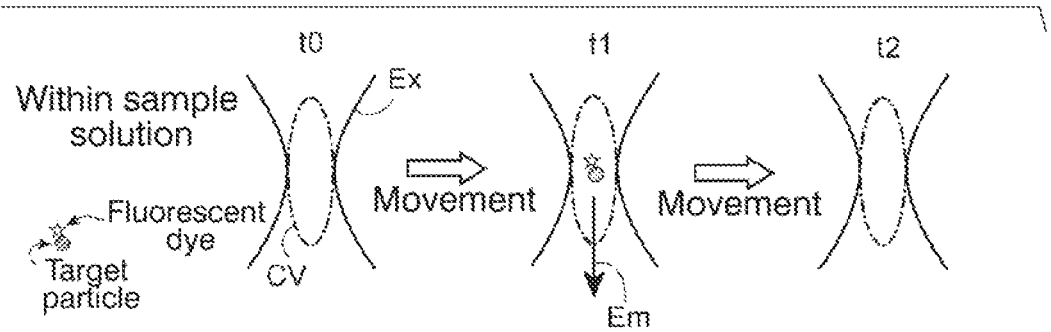
FIG. 2A is a schematic diagram explaining the principle of photodetection using optical analysis technology for a scanning molecule counting method.
Figure 2B:
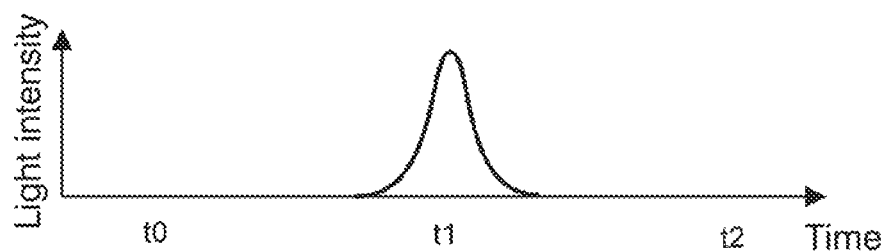
FIG. 2B is a schematic diagram of chronological changes in light intensity measured in FIG. 2A.

Processing carried out in the optical analysis technology of the scanning molecule counting method comprises carrying out photodetection by changing the light path by driving a mechanism (mirror light defector 17) for moving the location of the photodetection region while moving the location of the photodetection region CV in a sample solution. In other words, photodetection is carried out while scanning the interior of a sample solution by photodetection regions CV. In this case, as shown in FIG. 2A, for example, when a region is passed in which a single particle (a luminescent probe in the form of a fluorescent dye is bound to the particle in the drawings) is present (t1) during the time the photodetection region CV moves (time t0 to t2 in the drawings), significant light intensity (Em) is detected as shown in FIG. 2B. Movement of the location of the photodetection region CV and photodetection are carried out as described above, and particles bound with a luminescent probe are detected one at a time during that time. As a result, particles bound by the luminescent probe are individually detected and counted. As a result, the number of particles present in the measured region or information relating to concentration or number density can be acquired. In the principle of the optical analysis technology of the scanning molecule counting method, individual particles are detected without carrying out statistical arithmetic processing so as to determine fluctuations in fluorescence intensity. Thus, information relating to particle concentration or number density can be acquired even in a sample solution in which the concentration of particles to be observed is so low that they cannot be analyzed by FIDA and the like with adequate accuracy.

In addition, according to a method by which particles in a sample solution are individually detected and counted as in the scanning molecule counting method, measurements can be carried out at a lower concentration than in the case of measuring the concentration of fluorescent-labeled particles based on fluorescence intensity measured with a fluorescence spectrophotometer or plate reader. In the case of measuring the concentration of fluorescent-labeled particles with a fluorescence spectrophotometer or plate reader, fluorescence intensity is normally assumed to be proportional to the concentration of the fluorescent-labeled particles. In this case, however, if the concentration of the fluorescent-labeled particles becomes low enough, the amount of noise increases relative to the size of the signal generated from light emitted from the fluorescent-labeled particles (resulting in a poor S/N ratio), and the proportional relationship between the concentration of fluorescent-labeled particles and light signal strength is disrupted. As a result, the accuracy of determined concentration values becomes poor. In the scanning molecule counting method, noise signals are removed from the detection results in the step for detecting signals corresponding to individual particles from detected light signals, and concentration is calculated by counting only those signals corresponding to individual particles. Consequently, particles can be detected at a lower concentration than that in the case of detecting concentration based on the assumption of fluorescence intensity being proportional to the concentration of fluorescent-labeled particles.

Moreover, in the case a plurality of luminescent probes are bound to a single target particle, according to a method for individually detecting and counting particles in a sample solution in the manner of the scanning molecule counting method, particle concentration measurement accuracy can be improved for high particle concentrations to a greater degree than conventional methods consisting of determining concentration based on the assumption of fluorescence intensity being proportional to the concentration of fluorescent-labeled particles. In the case a plurality of luminescent probes bind to a single target particle, when a prescribed amount of luminescent probe is added to the sample solution, the number of luminescent probes that bind to the particles undergoes a relative decrease as the concentration of target particles increases. In this case, since the amount of fluorescence intensity per single target particle decreases, the proportional relationship between the concentration of fluorescent-labeled particles and the amount of light is disrupted. As a result, accuracy of determined concentration values becomes poor. In the scanning molecule counting method, in the detecting of signals corresponding to individual particles from detected light signals, concentration is calculated based on the number of particles with little effect of decreases in fluorescence intensity per particle. Consequently, particles can be detected at higher concentrations than in the case of detecting concentration based on the assumption that fluorescence intensity is proportional to the concentration of fluorescent-labeled particles.

<Measurement of Light Intensity of Sample Solution by Scanning Molecule Counting Method>

During measurement of light intensity in optical analyses using the scanning molecule counting method, the location of the photodetection region is moved in a sample solution by driving the mirror light deflector 17 during measurement (scanning the sample solution). Other processing may be carried out by an aspect similar to the fluorescence intensity measurement step of FCS or FIDA. During operational processing, sample solution is typically injected into the wells 10 of the microplate 9, and the microplate 9 is placed on the microscope stage. Subsequently, when a user inputs instructions for starting measurement to the computer 18, the computer 18 initiates radiation of excitation light and measurement of light intensity in a photodetection region in the sample solution in accordance with a program stored in a memory device (not shown)(consisting of a procedure for changing the light path so as to move the location of the photodetection region in the sample solution and a procedure for detecting light from the photodetection region during movement of the location of the photodetection region). During the aforementioned measurement, the mirror light deflector 17 drives the mirror 7 (galvanometer mirror) under the control of a processing operation in accordance with the program of the computer 18, and the location of the photodetection region is moved in the wells 10. At the same time, the photodetector 16 converts successively detected light to electrical signals and transmits those signals to the computer 18. In the computer 18, chronological light intensity data is generated from the transmitted light signals and stored therein. Furthermore, the photodetector 16 is typically an ultra-high-sensitivity photodetector capable of detecting the arrival of a single photon. Thus, light detection may be in the form of photon counting that is carried out in an aspect in which the number of photons arriving at the photodetector in a prescribed unit time period (bin time), such as every 10 µs, is successively measured over a prescribed amount of time. In addition, chronological light intensity data is in the form of chronological photon count data.

The movement speed when moving the location of the photodetection region during measurement of light intensity may be an arbitrary speed, and for example, may be a prescribed speed set experimentally or so as to comply with the analysis objective. In the case of acquiring information relating to number density or concentration based on the detected number of target particles, the region through which the photodetection region passes is required to have a certain size or volume. Thus, the location of the photodetection region is moved by a mode that allows movement distance to be determined. Furthermore, the presence of a proportional relationship between elapsed time during measurement and movement distance of the location of the photodetection region facilitates interpretation of measurement results. Consequently, movement speed may be basically made to be a constant speed, although not limited thereto.

Figure 3A:
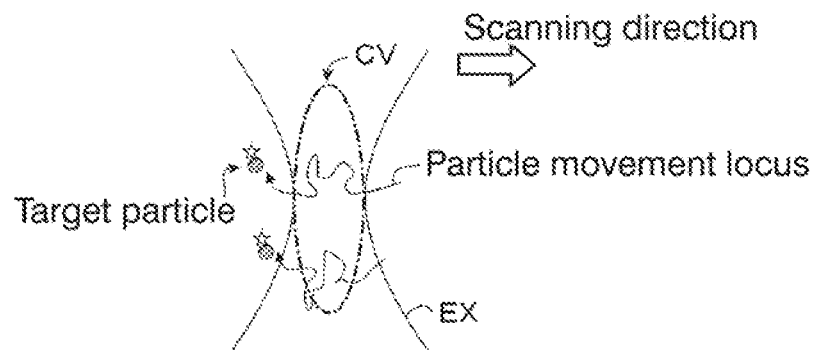
FIG. 3A is a model diagram of the case of target particles crossing a photodetection region while demonstrating Brownian movement.
Figure 3B:
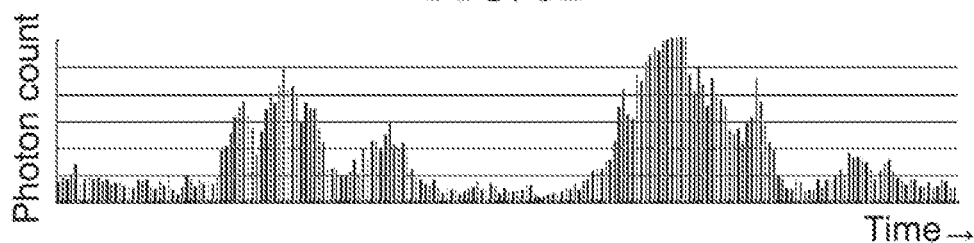
FIG. 3B is a drawing showing an example of chronological changes in photon count (light intensity) in FIG. 3A.
Figure 4A:
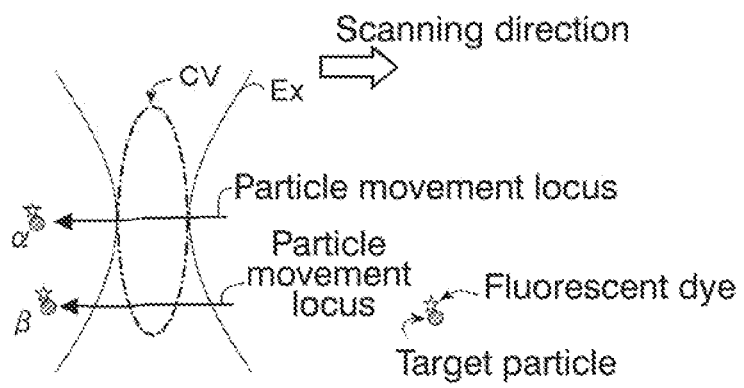
FIG. 4A is a model diagram of the case of target particles crossing a photodetection region by moving the location of the photodetection region in a sample solution at a speed faster than the diffusion movement speed of the target particles.
Figure 4B:
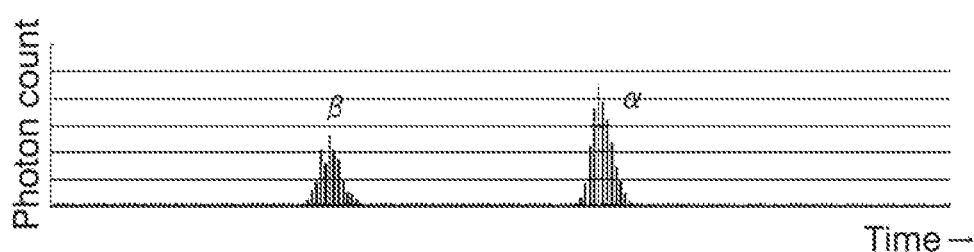
FIG. 4B is a drawing showing an example of chronological changes in photon count (light intensity) in FIG. 4A.

However, with respect to movement speed of the location of the photodetection region, in order to quantitatively detect individual target particles or count the number of target particles based on chronologically measured light intensity data with favorable accuracy, the aforementioned movement speed may be set to value that is faster than the random movement speed of the target particle (and more precisely, a conjugate of a particle and a luminescent probe or a luminescent probe that has degraded and been released after binding with the particle, and in the present embodiment, a target particle bound to a luminescent probe), or in other words, a speed faster than movement speed attributable to Brownian movement. Target particles in an optical analysis technology using the scanning molecule counting method are particles that are dispersed or dissolved in a solution and randomly move about freely therein. Consequently, their locations move over time by Brownian movement. Thus, in the case movement speed of the location of the photodetection region is slower than movement attributable to Brownian movement of the particles, the particles randomly move through the region as shown in FIG. 3A. As a result, light intensity changes randomly as shown in FIG. 3B (and excitation light intensity in the photodetection region peaks in the center of the region and then decreases moving towards the outside), and it becomes difficult to specify significant changes in light intensity corresponding to individual target particles. Consequently, particles may cross the photodetection region in nearly a straight line as shown in FIG. 4A. As a result, a profile of the change in light intensity corresponding to individual particles becomes nearly uniform as shown in FIG. 4B in the chronological light intensity data (in the case particles cross the photodetection region in nearly a straight line, the profile of changes in light intensity is roughly the same as the distribution of excitation light intensity). Namely, the movement speed of the location of the photodetection region is set to be faster than the average movement speed attributable to Brownian movement (diffusion movement speed) so that the correspondence between the individual target particles and light intensity can be easily determined.

More specifically, a time $\Delta t$ required for a target particle having a diffusion coefficient D (and more precisely, a conjugate of a particle and luminescent probe or a luminescent probe that has been degraded and released after binding with the particle) to pass through a photodetection region (confocal volume) having a diameter Wo by Brownian movement is obtained from the following relational expressions of mean square displacement of equations (1) and (2) below:

$$(2Wo)^2 = 6D \cdot \Delta t \quad (1)$$

$$\Delta t = (2Wo)^2 / 6D \quad (2)$$

The speed at which the target particle moves by Brownian movement (diffusion movement speed) Vdif is obtained from the following equation (3):

$$Vdif = 2Wo/\Delta t = 3D/Wo \quad (3)$$

The movement speed during movement of the location of the photodetection region is set to a value that is sufficiently faster than that speed by referring to Vdif. For example, in the case the diffusion coefficient D of a target particle is predicted to be about $2.0 \times 10^{-10}$ m$^2$/s, if Wo is taken to be about 0.62 μm, then Vdif becomes $1.0 \times 10^{-3}$ m/s. Consequently, the movement speed during movement of the location of the photodetection region is set to 15 mm/s, that is a value about 10 times greater than that. Furthermore, in the case the diffusion coefficient of a target particle is unknown, preliminary experiments are repeatedly carried out in order to find those conditions under which the prolife of changes in light intensity becomes the predicted profile (and typically, a prolife that is roughly the same as the excitation light distribution) by trying various settings for the movement speed during movement of the location of the photodetection region. As a result, a movement speed of the location of the photodetection region can be determined.

<Analysis of Light Intensity by Scanning Molecule Counting Method>

Once chronological light intensity data of a sample solution has been obtained according to the aforementioned processing, the computer 18 performs an analysis of light intensity in the manner described below by carrying out processing in accordance with a program stored in a memory device (consisting of a procedure for individually detecting light signals corresponding to individual luminescent particles from detected light).

(i) Detection of Single Target Particle

Figure 6A:
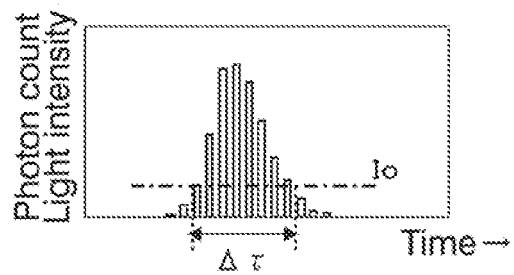
FIG. 6A is a drawing explaining an example of a signal processing of a detection signal in a processing procedure for counting particles based on chronological changes in photon count (light intensity) measured by a scanning molecule counting method.

In chronological light intensity data, in the case the locus when a single target particle passes through a photodetection region is roughly linear as shown in FIG. 4A, the change in light intensity corresponding to that particle has a profile (normally having a roughly bell-like shape) that reflects the distribution of light intensity in the photodetection region (determined by the optical system) as shown in FIG. 6A. In one technique for detecting a target particle, a threshold value Io is set for light intensity. When a duration $\Delta \tau$ during which light intensity continuously exceeds the threshold value Io is within a prescribed range, the profile of that light intensity is judged to correspond to the passage of a single particle through the photodetection region, and that single target particle is detected. The threshold value Io with respect to light intensity and the prescribed range with respect to duration $\Delta \tau$ are determined based on a profile presumed to be the intensity of light emitted from a conjugate of a target particle and luminescent probe (or a luminescent probe that has been degraded and separated after binding with that particle) that moves at a prescribed speed relative to the photodetection region. Specific values may be arbitrarily set experimentally, or may be selectively determined according to the properties of the conjugate of the target particle and luminescent probe (or a luminescent probe that has been degraded and released from the particle).

In addition, in another technique for detecting a target particle, when the distribution of light intensity of a photodetection region can be assumed to be a Gaussian distribution, the following equation (4) is satisfied:

$$I = A \cdot \exp(-2t^2/a^2) \quad (4)$$

Intensity A and width a are calculated by fitting equation (4) to a profile of significant light intensity (profile able to clearly determined to not be background). When the calculated intensity A and width a are within prescribed ranges, that light intensity profile is judged to correspond to the passage of a single target particle through the photodetection region, and a single target particle is detected (the profile is ignored as constituting noise or artifact during analysis when intensity A and width a are outside the prescribed ranges).

(ii) Counting of Target Particles

Counting of target particles may be carried out by counting the number of particles detected according to the aforementioned techniques for detecting target particles by an arbitrary method. However, in the case of a large number of particles, counting may be carried out according to processing shown in FIGS. 5 and 6B.

Figure 5:
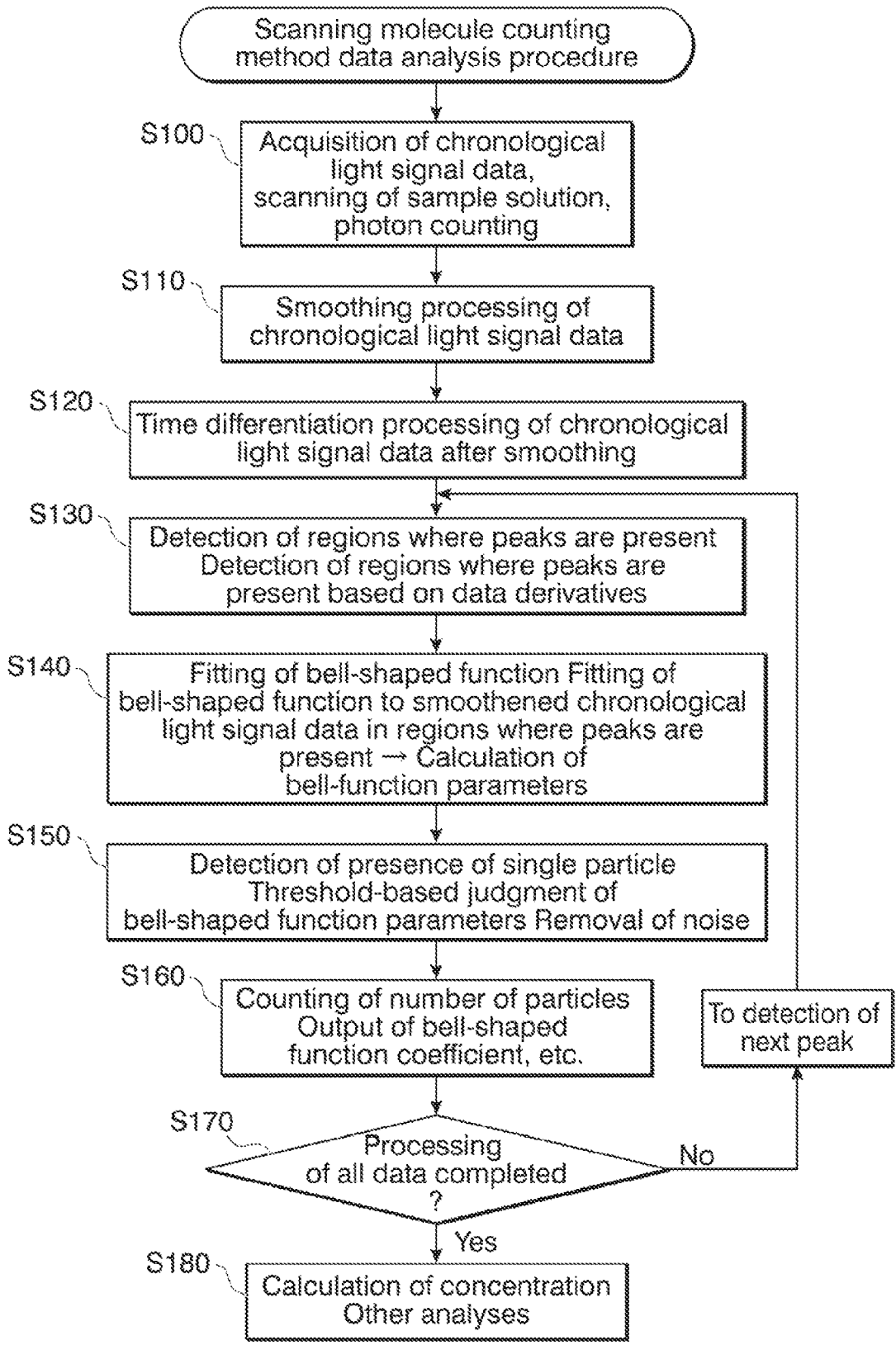
FIG. 5 is a drawing indicating a processing procedure for counting particles based on chronological changes in photon count (light intensity) measured by a scanning molecule counting method in the form of a flow chart.
Figure 6B:
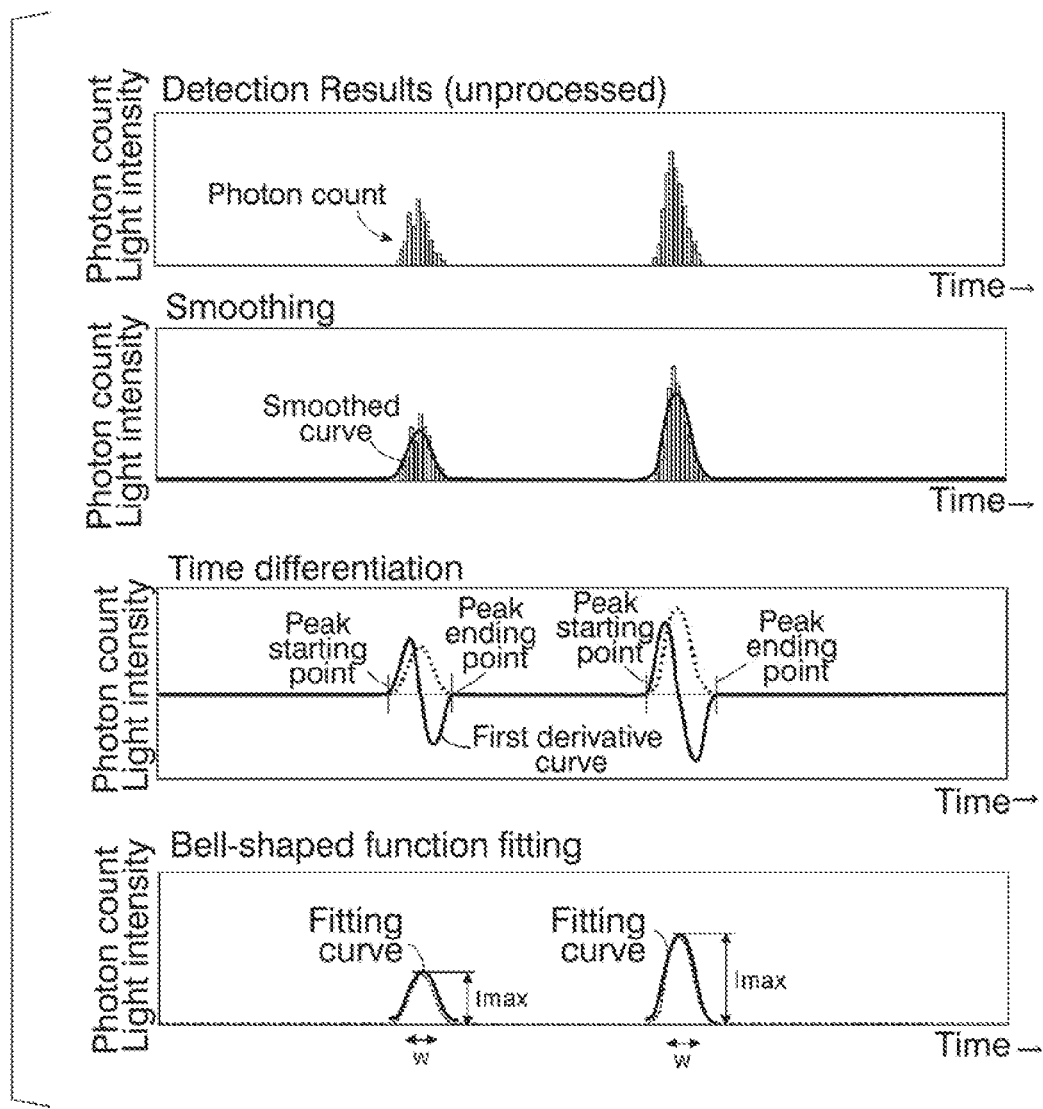
FIG. 6B is a drawing explaining an example of a signal processing of a detection signal in a processing procedure for counting particles based on chronological changes in photon count (light intensity) measured by a scanning molecule counting method.

As shown in FIGS. 5 and 6B, in one example of a method for counting particles from chronological light intensity (photon count) data, after having acquired chronological light signal data (photon count data) by carrying out measurement of light intensity as explained above, namely by carrying out scanning of a sample solution by photodetection regions and counting the number of photons (S 100), smoothing processing (S 110, "Smoothing" in FIG. 6B) is carried out on the chronological light signal data ("Detection result (unprocessed)" in FIG. 6B). Light emitted from conjugates of the particles and luminescent probe or that emitted from the luminescent probe is released statistically, thereby resulting in the possibility of omission of data values for minute time periods. Consequently, this smoothing processing makes it possible to ignore omission of data values as described above. Smoothing processing may be carried out by, for example, the moving average method. Furthermore, parameters used when carrying out smoothing processing (such as the number of data points averaged at one time, or the number of times movement is averaged in the moving average method) are suitably set corresponding to the movement speed of the location of the photodetection region when acquiring light intensity data (scanning speed) and bin time.

Next, in order to detect a time region in which a significant signal is present (peak region) in chronological light signal data following smoothing processing, a first derivative is calculated for the time of the chronological light signal data following smoothing processing (S 120). The change in the time derivative of chronological light signal data increases at the inflection point of the signal value as indicated by "Time differentiation" in FIG. 6B. Thus, the starting point and ending point of a significant signal (peak signal) can be advantageously determined by referring to this time derivative.

Subsequently, significant signals (peak signals) are successively detected in the chronological light signal data, and a judgment is made as to whether or not the detected peak signals are signals corresponding to target particles.

Figure 7:
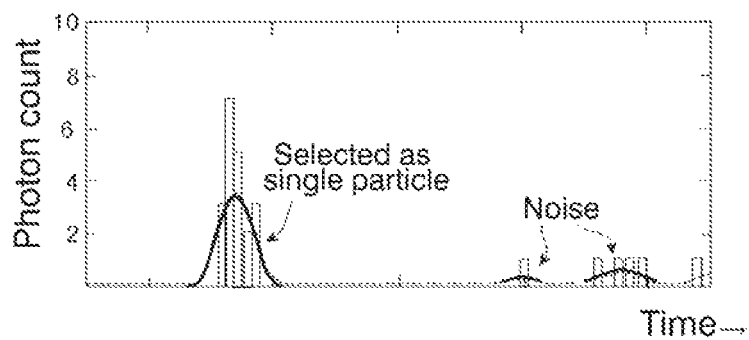
FIG. 7 indicates an example of actual measurements of photon count data measured by a scanning molecule counting method (bar graph), a curve obtained by smoothing the data (dotted line), and a Gaussian function fit to those regions where peaks are present (solid line) (in the drawing, signals indicated as being "noise" are ignored as signals attributable to noise or artifacts).

More specifically, a peak region is identified by searching for and determining the starting point and ending point of a single peak signal by successively referring to time derivatives in the chronological time-differentiated data of the chronological light signal data (S 130). Once a single peak region has been identified, a bell-shaped function is fit to the smoothened chronological light signal data in that peak region (Bell-shaped function fitting" in FIG. 6B). As a result, parameters such as peak intensity Imax of the bell-shaped function, peak width (half width at maximum) w and correlation coefficient (of the least squares method) during fitting are calculated (S 140). Furthermore, although the bell-shaped function subjected to fitting is typically a Gaussian function, it may also be a Lorentzian function. A judgment is then made as to whether or not the calculated bell-shaped function parameters are within a presumed range for the parameters of a bell-shaped profile depicted by a light signal detected when a single conjugate of a particle and luminescent probe or luminescent probe has passed through a photodetection region. Namely, a judgment is made as to whether or not peak intensity, peak width and correlation coefficient are each within a prescribed range (S 150). A signal for which calculated bell-shaped function parameters have been judged to be within the presumed ranges for a light signal corresponding to a single conjugate of a particle and luminescent probe or luminescent probe as indicated on the left side of FIG. 7 is judged to be a signal corresponding to a single target particle. As a result, a single target particle is detected and that target particle is counted as a single particle (and the particle count is incremented by 1, S 160). On the other hand, peak signals in which the calculated bell-shaped function parameters are not within the presumed ranges as indicated on the right side of FIG. 7 are ignored as constituting noise.

The searching and discrimination of peak signals in the aforementioned processing of steps 130 to 160 are carried out repeatedly for the entire range of chronological light signal data, and each time a single target particle is detected, that target particle is counted as a particle. When searching for peak signals throughout the entire range of chronological light signal data has been completed (S 170), the particle count value obtained up to that time is taken to be the number of target particles detected in the chronological light signal data.

(iii) Determination of Number Density and Concentration of Target Particles

When target particles are counted, the number density or concentration of the target particles is determined using the total volume of the region of the photodetection region traversed during acquisition of chronological light signal data. However, the effective volume of the photodetection region fluctuates dependent upon the wavelength of the excitation light or detection light, numerical aperture of the lens, and adjustment state of the optical system. Consequently, it is generally difficult to determine the effective volume of the photodetection region from design values. In addition, it is also not easy to determine the total volume of the region of the photodetection region traversed by target particles. Thus, light intensity is typically measured and particles are detected and counted as previously explained for a solution having a known particle concentration (reference solution) under the same conditions as those used when measuring a sample solution to be tested. The total volume of the traversed region of the photodetection region, namely the relationship between the detected number and concentration of target particles, may be determined from the number of detected particles and the particle concentration of the reference solution.

The particles of the reference solution may consist of a fluorescent label (such as a fluorescent dye) having luminescent properties similar to conjugates of particles and luminescent probe formed by the target particles (or luminescent probe that has released after binding with the target particles). More specifically, when assuming a number of detected particles N for a reference solution having a particle concentration C, for example, then the total volume Vt of the traversed region of the photodetection region is obtained from the following equation (5):

$$Vt=N/C \qquad (5)$$

In addition, a plurality of solutions having different concentrations may be provided for use as reference solutions, measurements may be carried out on each reference solution, and the average value of the calculated Vt may be used as the total volume Vt of the traversed region of the photodetection region. If Vt is given, then the number density c of particles in a sample solution for which the result of particle counting is n is obtained from the following equation (6):

$$c=n/Vt \qquad (6)$$

Furthermore, the volume of a photodetection region and the total volume of the traversed region of the photodetection region are not limited to being determined according to the aforementioned method, but rather may also be determined by using an arbitrary method such as FCS or FIDA. In addition, in the optical analysis device of the present embodiment, information on the relationship between concentration C and particle count N (Equation (5)) for various standard particles for presumed photodetection region movement patterns is preliminarily stored in a memory device of the computer 18. As a result, suitably stored relationship information may be able to be used when optical analyses are performed by a device user.

<Target Particle Detection Method>

The method for detecting a target particle of the present embodiment is a method for detecting a target particle dispersed and randomly moving in a sample solution. A target particle in a sample solution is labeled by binding with a luminescent probe so that luminescence intensity per molecule is greater than the free luminescent probe. Subsequently, a target particle bound to the luminescent probe is detected according to the scanning molecule counting method. The scanning molecule counting method is a measurement method that enables luminescent particles to be measured one particle at a time while molecules are in a discrete state. Namely, measurements can be carried out even on luminescent particles at a comparatively low concentration on the pM order or lower. Consequently, even in cases in which the concentration of target particles to be analyzed in a sample solution is extremely low, the method for detecting a target particle of the present embodiment can be used to count a target particle bound to a luminescent probe with high sensitivity. Moreover, in the method for detecting a target particle of the present embodiment, luminescence intensity per molecule of luminescent probe bound to a target particle is greater than the luminescence intensity per molecule of free luminescent probe. Consequently, a target particle can be detected by distinguishing between a luminescent probe bound to a target particle and a free luminescent probe, without having to preliminarily remove the free luminescent probe from the sample solution prior to measurement by the scanning molecule counting method.

More specifically, the method for quantifying a target particle of the present embodiment is provided with the following (a) and (b):

(a) preparing a sample solution containing a target particle and one type or two or more types of a luminescent probe that binds to the target particle, and allowing two or more molecules of the luminescent probe to bind per one molecule of the target particle in the sample solution, and (b) calculating the number of molecules of target particles bound to the luminescent probe present in the sample solution prepared in (a).

The following provides an explanation of the (a) and (b).

First, in (a), a sample solution containing the target particle and one type or two or more types of a luminescent probe that binds to the target particle is prepared, and two or more molecules of the luminescent probe are allowed to bind per one molecule of the target particle in the sample solution.

In the present embodiment, "particles dispersed and moving randomly in a sample solution" refer to particles such as atoms, molecules or aggregates thereof dispersed or dissolved in a sample solution (and may be particles that emit light or particles that do not emit light) that move about freely by Brownian movement in a solution without being immobilized on a substrate and the like.

The target particles refer to particles that are dispersed and moving randomly in a sample solution and are targeted for detection in the sample solution. Examples of target particles include biomolecules such as proteins, peptides, nucleic acids, nucleic acid-like substances, lipids, saccharides, amino acids or aggregates thereof, particulate biological targets such as viruses or cells, and non-biological particles (such as atoms, molecules, micelles or metal colloids). Nucleic acids may be DNA or RNA, or may be artificially amplified substances in the manner of cDNA. Examples of nucleic acid-like substances include substances in which side chains and the like of naturally-occurring nucleotides in the manner of DNA or RNA (nucleotides present in nature) have been modified by functional groups such as an amino group, and substances that have been labeled with a protein or low molecular weight compound and the like. Specific examples of nucleic acid-like substances include bridged nucleic acids (BNA), nucleotides in which an oxygen atom at position 4' of a naturally-occurring nucleotide has been substituted with a sulfur atom, nucleotides in which a hydroxyl group at position 2' of a naturally-occurring nucleotide has been substituted with a methoxy group, hexitol nucleic acids (HNA) and peptide nucleic acids (PNA).

A luminescent probe used in the present embodiment is a substance that emits light and has a site that specifically or non-specifically binds or adsorbs to a target particle. A luminescent probe can be produced by allowing a luminescent substance to bind to a substance that specifically or non-specifically binds or adsorbs to a target particle (labeling probe). Although the luminescent substance is typically a fluorescent substance, it may also be a substance that emits light by phosphorescence, chemiluminescence, bioluminescence or light scattering.

There are no particular limitations on the fluorescent substance provided it is a substance that releases fluorescence as a result of being irradiated with light of a specific wavelength. The fluorescent substance can be used by suitably selecting from among fluorescent dyes or quantum dots and the like used in FCS or FIDA and the like. A fluorescent substance may be used as a luminescent substance in the present embodiment from the advantage of allowing detection with higher sensitivity.

For example, in the case the target particle is a nucleic acid or nucleic acid-like substance, examples of the luminescent probe include a substance in which a luminescent substance such as a fluorescent substance is bound to an oligonucleotide that hybridizes with the target particle, a nucleic acid-binding protein bound with a luminescent substance such as a fluorescent substance, and a dye molecule that binds to nucleic acid. The aforementioned oligonucleotide may be DNA, RNA or an artificially amplified substance in the manner of cDNA, or a substance that contains a portion or all of a nucleic acid-like substance capable of forming a nucleotide chain and base pairs in the same manner as naturally-occurring nucleic acid bases. In addition, in the case the target particle is a protein, a substance in which an antigen or antibody to the target particle or a ligand or receptor for the target particle is labeled with a luminescent substance such as a fluorescent substance can be used as a luminescent probe. Furthermore, binding of a luminescent substance to a substance that specifically or non-specifically binds or adsorbs to a target particle such as a nucleic acid or protein can be carried out by ordinary methods.

The luminescent probe may be that in which a labeling probe and luminescent substance are directly bound by covalent bonding and the like, or that in which a labeling probe and a luminescent substance are bound by a specific binding reaction such as an antigen-antibody reaction or ligand and receptor binding reaction. For example, that in which a labeling probe bound to biotin and a luminescent substance bound to streptavidin are bound through a biotin-streptavidin binding reaction can be used as a luminescent probe. More specifically, in the case the target particle is a nucleic acid or nucleic acid-like substance, that in which a substance binding to an oligonucleotide that hybridizes with a target particle and biotin is bound to a luminescent substance bound to streptavidin can be used as a luminescent probe. In addition, in the case the target particle is a protein, that in which a substance in which biotin is bound to a ligand or receptor for a target particle is bound with a luminescent substance bound to streptavidin can be used as a luminescent probe.

The luminescent probe may be that in which one molecule of a labeling probe is bound to one molecule of a luminescent substance by a specific binding reaction, or may be that in which one molecule of a labeling probe is bound to two or more molecules of a luminescent substance by a specific binding reaction. For example, the luminescent probe may be that in which a labeling probe having a single biotin site and a luminescent substance bound to streptavidin are bound through a biotin-streptavidin binding reaction. In addition, the luminescent probe may be that in which a labeling probe having two or more biotin sites is bound with a luminescent substance bound to streptavidin.

Although the luminescent probe used in the present embodiment may be a substance that non-specifically binds to a target particle, from the viewpoint of accuracy of detection and quantitative determination of target particles, it may be a substance that binds specifically to the particle. Furthermore, the luminescent probe that specifically binds to a target particle is only required to be a substance that preferentially binds to the target particle rather than binding to other substances having physical or chemical properties similar to those of the target particle. Namely, the aforementioned luminescent probe is not required to be a substance that does not bind at all to substances other than the target particle. For example, in the case the target particle is a nucleic acid, an oligonucleotide labeled with a luminescent substance used as a luminescent probe may have a base sequence that is completely complementary to the base sequence of the target particle, or may have a base sequence that contains mismatches with the base sequence of the target particle.

One type or two or more types of luminescent probes may be used for the luminescent probe used in the present embodiment. However, all luminescent probes added to a sample solution emit light from the same type of luminescent substance. For example, in the case the target particle is a nucleic acid or nucleic acid-like substance, a first luminescent probe, in which a luminescent substance such as a fluorescent substance is bound to a first oligonucleotide that binds to a target particle, and a second luminescent probe, in which a luminescent substance of the same type as the first luminescent probe is bound to a second oligonucleotide that hybridizes with the target particle in a region differing from that of the first oligonucleotide, can be used together. In this case, the target particle in a sample solution is present as a particle in which the first luminescent probe, the second luminescent probe and the target particle are bound. Namely, two molecules of luminescent substance are contained per particle in particles containing the target particles. Consequently, a stronger light signal is detected by the scanning molecule counting method from particles containing the target particles than from the free first luminescent probe and second luminescent probe.

More specifically, in (a), a sample solution is prepared by adding a target particle and one type or two or more types of a luminescent probe to a suitable solvent. There are no particular limitations on the solvent provided it does not inhibit detection of light released from a luminescent probe bound to the target particle or inhibit detection of the luminescent probe bound to the target particle by the scanning molecule counting method. The solvent can be suitably selected and used from among buffers commonly used in the aforementioned technical field. Examples of the aforementioned buffers include phosphate buffers or Tris buffers such as phosphate-buffered saline (PBS, pH 7.4).

In the case of being able to bind both the target particle and luminescent probe simply by having both present in the same solution, the sample solution is incubated as necessary for a prescribed amount of time after preparing the sample solution. The target particle and luminescent probe can be bound in the aforementioned sample solution simply by carrying out the aforementioned method.

On the other hand, in the case the target particle or luminescent probe is a nucleic acid molecule or nucleic acid-like substance having a double-stranded structure, the target particle and luminescent probe may be associated after having denatured the nucleic acid and the like in the sample solution. Furthermore, "denaturing a nucleic acid molecule or nucleic acid-like substance" refers to dissociation of base pairs. For example, this refers to dissociating base pairs formed by mutually complementary base sequences in a molecular beacon probe to disassemble an intramolecular structure and form a single-stranded structure, or converting a double-stranded nucleic acid molecule into a single-stranded nucleic acid molecule. Furthermore, in the case the luminescent probe is an oligonucleotide containing a nucleic acid-like substance such as PNA, there are cases in which an association product consisting of the luminescent probe and target particle can be formed without having to carry out a special denaturation treatment even if the target particle was in the form of a double-stranded nucleic acid molecule.

Examples of denaturation treatment include denaturation by high-temperature treatment (heat denaturation) and denaturation by low salt concentration treatment. Heat denaturation may be carried out for the aforementioned denaturation treatment since it has the advantages of having comparatively little effect on a fluorescent substance or other luminescent substance and having a simple procedure. More specifically, in the case of heat denaturation, nucleic acid and the like in a sample solution can be denatured by subjecting the sample solution to high-temperature treatment. In general, denaturation can be carried out by holding at a temperature of 90° C. for DNA or 70° C. for RNA for several seconds to about 2 minutes. However, the denaturing temperature varies according to the base length of the target particle and the like. Thus, the temperature is not limited thereto provided denaturation is possible at that temperature. On the other hand, denaturation by low salt concentration treatment can be carried out by, for example, adjusting the salt concentration of the sample solution to be sufficiently low by diluting with purified water and the like.

After having carried out denaturation as necessary, the target particle and luminescent probe in the aforementioned sample solution are allowed to associate.

In the case of having carried out heat denaturation, the temperature of the sample solution is lowered to a temperature that allows specific hybridization between the target particle and luminescent probe following high-temperature treatment. As a result, the target particle and luminescent probe in the sample solution can be suitably associated. In addition, in the case of having carried out denaturation by low salt concentration treatment, the salt concentration of the sample solution is raised to a concentration that allows specific hybridization between the target particle and luminescent probe by adding a salt solution. As a result, the target particle and luminescent probe in the sample solution can be suitably associated.

Furthermore, the temperature at which two single-stranded nucleic acid molecules are able to specifically hybridize can be determined from a melting curve of an association product of the two. A melting curve can be determined by, for example, changing the temperature of a solution containing only the two single-stranded nucleic acid molecules from a high temperature to a low temperature, and measuring optical absorbance or fluorescence intensity of the aforementioned solution. The temperature range from the temperature at which the two denatured single-stranded nucleic acid molecules begin to form an association product to the temperature at which the nucleic acid molecules have nearly completely formed an association product as determined from the resulting melting curve can be taken to be the temperature at which both specifically hybridize. The concentration at which two single-stranded nucleic acid molecules are able to specifically hybridize can be determined by similarly determining a melting curve by changing the salt concentration in the solution from a low concentration to a high concentration instead of changing the temperature.

The temperature at which two single-stranded nucleic acid molecules specifically hybridize can generally be substituted for the Tm value (melting temperature). For example, commonly used primer/probe design software can be used. As a result, the Tm value of a region that hybridizes with a target particle (temperature at which 50% of double-stranded DNA dissociates to single-stranded DNA) can be calculated from base sequence information of the luminescent probe.

In addition, in order to suppress non-specific hybridization, the temperature of the sample solution may be lowered comparatively slowly when forming an association product. For example, after having denatured a nucleic acid molecule by raising the temperature of a sample solution to 70° C. or higher, the liquid temperature of the sample solution can be lowered at a temperature lowering rate of 0.05° C./second or higher.

In addition, in order to inhibit non-specific hybridization, a surfactant, formamide, dimethylsulfoxide or urea and the like may be added to the sample solution in advance. Only one type of these compounds may be added or two or more types may be added in combination. The addition of these compounds makes it possible to reduce the likelihood of the occurrence of non-specific hybridization in a comparatively low temperature environment.

Subsequently, in (b), the number of molecules of target particles bound to the luminescent probe present in the prepared sample solution is counted. More specifically, a sample solution following binding of the target particles to a luminescent probe is installed in an optical analysis device for the aforementioned scanning molecule counting method, and the number of target molecules bound to the luminescent probe is counted by detecting and analyzing light released from the luminescent probe in a state of being bound to the target particles according to the previously described method. The counted number of target particles is the number of target particles contained in the measurement sample.

The target particles in the sample solution bind to two or more molecules of luminescent probe per molecule thereof. Consequently, the strength of a light signal per target particle bound to the luminescent probe is stronger than that of the free luminescent probe (namely, particles having one molecule of luminescent probe per particle). Consequently, whether individually detected particles are target particles bound to the luminescent probe or the free luminescent probe can be distinguished by using light signal strength as an indicator. The number of target particles can be counted by counting only those particles in which two or more molecules of luminescent probe are contained per particle. For example, a solution containing only luminescent probe is prepared in advance, and the number of molecules of luminescent probe in the aforementioned solution is counted by the scanning molecule counting method. As a result, it is possible to count only the target particles by measuring the light signal strength per molecule of free luminescent probe, and setting a suitable threshold value so that the light signal strength detected from the free luminescent probe is not included therein.

EXAMPLES

Although the following provides a more detailed explanation of the present invention by indicating examples and the like thereof, the present invention is not limited to the following examples.

Example 1

Target particles in a sample solution were detected by the scanning molecule counting method using a substance having a large number of biotinylation sites per molecule for the target particles and using a quantum dot bound with streptavidin for the luminescent probe.

<Case of Using Double-Stranded Nucleic Acid Molecule as Target Particle>

A double-stranded nucleic acid molecule having a large number of biotinylation sites per molecule was used for the target particle.

More specifically, PCR was carried out using dNTP containing biotin-labeled dCTP and plasmid pUC19 as template, and the 800 bp PCR product was used for the target particle. More specifically, the aforementioned PCR was carried out using Takara ExTaq (Takara Bio Inc.) as heat-resistant polymerase under temperature cycling conditions consisting of initially treating for 5 minutes at 95° C., followed by 40 cycles consisting of 30 seconds at 95° C., 30 seconds at 50° C. and 1 minute at 68° C., and finally treating for 10 minutes at 68° C. The resulting PCR product was purified using the Wizard SV Clean Up Kit (Promega Corp.). The purified PCR product was electrophoresed using an electrophoresis system (Agilent Technologies, Inc.), and the specimen was adjusted to 2 nM based on the converted concentration.

The resulting PCR product and 20 nM streptavidin-bound Qdot® 655 solution (Streptavidin-Bound Qdot® (Invitrogen Corp.) diluted with STEP buffer) were mixed at a 1:1 ratio (volume ratio) to prepare a sample solution. After allowing the aforementioned sample solution to stand undisturbed for 30 minutes, the sample solution was diluted 50-fold using STEP buffer followed by further diluting 20-fold and measuring by the scanning molecule counting method.

In addition, a solution obtained by similarly diluting the aforementioned streptavidin-bound Qdot® 655 solution with STEP buffer was measured as a reference.

More specifically, the MF20 Single Molecule Fluorescence Spectroscopy System (Olympus Corp.) equipped with a confocal fluorescent microscope optical system and photon counting system was used as an optical analysis device during measurement, and time series photon count data was acquired for each of the aforementioned sample solutions. At that time, laser light having a wavelength of 488 nm was used as excitation light, laser light was irradiated at 300 µW, and the detecting light wavelength was set to 650 nm to 690 nm using a band pass filter. Signals obtained from an avalanche diode were set to a bin time of 10 µs, and measurement time was set to 20 seconds.

After smoothing the chronological data obtained from the measurements using the Savinzky-Golay algorithm, peaks were detected by differentiation. Those regions considered to be peaks that were able to be approximated to a Gaussian function were extracted as signals.

The measurement results are shown in Table 1. In Table 1, "Qdot Ref" indicates the results of measuring only the Streptavidin-Bound Qdot® 655 solution, while "xBiotin-PCR" indicates the results of measuring the sample solution containing the aforementioned PCR product and the Streptavidin-Bound Qdot® 655. As a result, the aforementioned PCR product having a large number of biotinylation sites per molecule and in which a large number of Streptavidin-Bound Qdot® 655 were bound per molecule allowed the obtaining of a stronger signal in comparison with the free Streptavidin-Bound Qdot® 655, and a definite difference in signal strength was observed between the two. Namely, the aforementioned PCR product bound to Streptavidin-Bound Qdot® 655 was determined to be able to be detected as a result of being able to be distinguished from free Streptavidin-Bound Qdot® 655.

TABLE 1

|  | Photon Count | No. of Peaks | Max. Light signal Strength |
|---|---|---|---|
| Qdot-Ref | 70330 | 57 | 2.40 |
| xBiotin-PCR | 112155 | 1608 | 12.58 |

<Case of Using Dextran as Target Particle>

Biotinylated dextran (Invitrogen Corp.) having a large number of biotinylation sites per molecule was used for the target particle.

More specifically, biotinylated dextran at a final concentration of 1 nM and Streptavidin-Bound Qdot® 655 (Invitrogen Corp.) at a final concentration of 10 nM were respectively added to PBS buffer to prepare a sample solution. After allowing the aforementioned sample solution to stand undisturbed for 30 minutes, a solution obtained by diluting 100-fold using PBS buffer (Streptavidin-Bound Qdot® 655 concentration: 10 pM) was measured by the scanning molecule counting method.

In addition, a solution obtained by adding only Streptavidin-Bound Qdot® 655 without adding biotinylated dextran was similarly diluted with PBS buffer and measured as a reference.

Measurement by the scanning molecule counting method was carried out in the same manner as in the case of using a double-stranded nucleic acid molecule for the target particle as previously described.

The measurement results are shown in Table 2. In Table 2, "Qdot Ref" indicates the results of measuring only the Streptavidin-Bound Qdot® 655 solution, while "xBiotin-Dex" indicates the results of measuring the sample solution containing the biotinylated dextran and the Streptavidin-Bound Qdot® 655. As a result, the biotinylated dextran having a large number of biotinylation sites per molecule and in which a large number of Streptavidin-Bound Qdot® 655 were bound per molecule allowed the obtaining of a stronger signal in comparison with the free Streptavidin-Bound Qdot® 655, and a definite difference in signal strength was observed between the two. Namely, the aforementioned biotinylated dextran bound to Streptavidin-Bound Qdot® 655 was determined to be able to be detected as a result of being able to be distinguished from free Streptavidin-Bound Qdot® 655.

TABLE 2

|  | Photon Count | No. of Peaks | Max. Light signal Strength |
|---|---|---|---|
| Qdot-Ref | 70330 | 57 | 2.40 |
| xBiotin-Dex | 81733 | 178 | 7.27 |

<Case of Setting Light Signal Threshold Value to 3.0>

Since the light signal strength of free Streptavidin-Bound Qdot® 655 was 2.40, the threshold value of light signal strength was set to 3.0, and only the number of peaks having a value of 3.0 or higher were counted as target particles (the aforementioned PCR product or biotinylated dextran) bound to the luminescent probe (Streptavidin-Bound Qdot® 655). The counting results are shown in Table 3. As a result, the frequency at which peaks having light signal strength of 3.0 or higher was higher for the solution containing the aforementioned PCR product or biotinylated dextran and Streptavidin-Bound Qdot® 655 than the solution containing only Streptavidin-Bound Qdot® 655 serving as a reference.

TABLE 3

|  | No. of Peaks | SD |
|---|---|---|
| Qdot Ref | 0 | — |
| xBiotin-PCR | 64 | 16 |
| xBiotin-Dex | 39 | 9 |

Example 2

Target particles in a sample solution were detected by the scanning molecule counting method using biotinylated dextran having two biotinylation sites per molecule (Invitrogen Corp.) for the target particles and using a quantum dot bound with streptavidin for the luminescent probe.

More specifically, biotinylated dextran at a final concentration of 2 nM and Streptavidin-Bound Qdot® 655 (Invitrogen Corp.) at a final concentration of 10 nM were respectively added to PBS buffer to prepare a sample solution. After allowing the aforementioned sample solution to stand undisturbed for 30 minutes, a solution obtained by diluting 1000-fold using PBS buffer was measured by the scanning molecule counting method.

In addition, a solution obtained by adding only Streptavidin-Bound Qdot® 655 without adding biotinylated dextran was similarly diluted with PBS buffer and measured as a reference.

Measurement by the scanning molecule counting method was carried out in the same manner as Example 1 with the exception of irradiating with excitation light at 1 mW.

The measurement results are shown in Table 4. In Table 4, "Qdot Ref" indicates the results of measuring only the Streptavidin-Bound Qdot® 655 solution, while "xBiotin-Dex" indicates the results of measuring the sample solution containing the biotinylated dextran and the Streptavidin-Bound Qdot® 655. As a result, the biotinylated dextran having two biotinylation sites per molecule and in which two molecules of Streptavidin-Bound Qdot® 655 were bound per molecule allowed the obtaining of signal having roughly twice the signal strength of the free Streptavidin-Bound Qdot® 655, and a definite difference in signal strength was observed between the two. Namely, the biotinylated dextran bound to Streptavidin-Bound Qdot® 655 was determined to be able to be detected as a result of being able to be distinguished from free Streptavidin-Bound Qdot® 655.

TABLE 4

|  | Photon Count | No. of Peaks | Max. Light signal Strength |
|---|---|---|---|
| Qdot-Ref | 13295 | 19 | 6.37 |
| xBiotin-Dex | 12141 | 16 | 13.64 |

In the scanning molecule counting method used in the method for detecting a target particle according to the examples shown above, statistical processing involving the calculation of fluctuations in fluorescence intensity is not carried out. Consequently, according to the method for detecting a target particle according to above-shown examples, the target particle in a sample can be detected even in cases in which the target particle to be analyzed are only present in a sample in a trace amount. Moreover, in the method for detecting a target particle according to the examples shown above, the luminescence intensity per molecule of luminescent probe bound to a target particle is greater than the luminescence intensity per molecule of free luminescent probe. Consequently, a target particle can be detected by distinguishing between the luminescent probe bound to a target particle and free luminescent probe without having to preliminarily remove the free luminescent probe from the sample solution prior to measurement by the scanning molecule counting method as shown in the examples.

BRIEF DESCRIPTION OF THE REFERENCE SYMBOLS

1 Optical analysis device (confocal microscope)
2 Light source
3 Single-mode optic fiber
4 Collimator lens
5 Dichroic mirror
6,7,11 Reflecting mirror
8 Object lens
9 Microplate
10 Well (sample solution container)
12 Condenser lens
13 Pinhole
14 Barrier filter
15 Multi-mode optic fiber
16 Photodetector
17 Mirror light deflector
17a Stage position adjustment device
18 Computer

The invention claimed is:

1. A method for detecting a target particle dispersed and moving randomly in a sample solution, comprising:
   (a) preparing a sample solution containing the target particle and luminescent probes, and allowing two or more luminescent probes to bind per one target particle in the sample solution,
   (b) moving a location of a photodetection region of an optical system of a confocal microscope or a multiphoton microscope in the sample solution,
   (c) detecting light from the photodetection region during the moving of the location of the photodetection region in the sample solution over a plurality of units of time, and generating time series light intensity data of the light from the light detection region detected while moving the position of the light detection region in the sample solution,
   (d) smoothing data values corresponding to light intensity variation over the plurality of units of time of a light signal from the luminescent probes bound to each target particle, said smoothing being conducted until a gap in the light intensity variation can be disregarded,
   (e) individually detecting the target particle bound to the luminescent probes when the light intensity variation in the time series light intensity data over consecutive units among the plurality of units of time has a predetermined profile which is expected from a single light-emitting particle moving relatively inside the photodetection region, and
   (f) counting the number of the target particles by using the light intensity of the target particle detected in the step (e) as an indicator thereof.

2. The method for detecting a target particle according to claim 1, wherein, in the moving of the location of the photodetection region, the location of the photodetection region is moved at a prescribed speed.

3. The method for detecting a target particle according to claim 1, wherein, in the moving of the location of the photodetection region, the location of the photodetection region is moved at a speed that is faster than the diffusion movement speed of the target particle bound to the luminescent probe.

4. The method for detecting a target particle according to claim 1,
   wherein, in the individually detecting of the target particles by detecting a light signal from the individual target particle from the detected light, the entry of a single target particle bound to the luminescent probes into the photodetection region is detected based on the form of a chronologically detected light signal.

5. The method for detecting a target particle according to claim 1, wherein the luminescent probes comprise a labeling probe that binds with the target particle and a luminescent substance of which one or more substances bind per one labeling probe.

* * * * *